US005962316A

United States Patent [19]
Beach et al.

[11] Patent Number: 5,962,316
[45] Date of Patent: Oct. 5, 1999

[54] CELL-CYCLE REGULATORY PROTEINS, AND USES RELATED THERETO

[75] Inventors: David H. Beach, Huntington Bay; Douglas J. Demetrick, Northport; Manuel Serrano, Mill Neck; Gregory J. Hannon, Huntington, all of N.Y.

[73] Assignee: Cold Spring Harbor Laboratory, Cold Spring Harbor, N.Y.

[21] Appl. No.: 08/306,511

[22] Filed: Sep. 14, 1994

Related U.S. Application Data

[63] Continuation-in-part of application No. 08/248,812, May 25, 1994, which is a continuation-in-part of application No. 08/227,371, Apr. 14, 1994, which is a continuation-in-part of application No. 08/154,915, Nov. 18, 1993, which is a continuation-in-part of application No. 07/991,997, Dec. 17, 1992, abandoned, which is a continuation-in-part of application No. 07/963,308, Oct. 16, 1992.

[51] Int. Cl.$^6$ .................................................. C12N 15/00
[52] U.S. Cl. ...................... 435/325; 435/320.1; 435/69.1; 435/455; 435/6; 536/23.1; 536/24.1; 536/23.4; 536/23.5; 514/44; 424/93.21; 424/185.1; 530/350
[58] Field of Search ............................... 514/44; 530/350; 435/69.1, 320.1, 172.3, 455, 6; 424/185.1, 93.21; 536/23.1, 23.5, 23.4

[56] References Cited

FOREIGN PATENT DOCUMENTS

| | | |
|---|---|---|
| WO 91/16429 | 10/1991 | WIPO . |
| WO 92/06180 | 4/1992 | WIPO . |
| WO 92/19749 | 11/1992 | WIPO . |
| WO 92/20316 | 11/1992 | WIPO . |
| WO 92/22635 | 12/1992 | WIPO . |
| WO 93/04701 | 3/1993 | WIPO . |
| WO 93/15227 | 8/1993 | WIPO . |
| WO 94/09135 | 4/1994 | WIPO . |

OTHER PUBLICATIONS

Wallace et al. Methods in Enzymology 1987, 152:432.
Sambrook et al. Molecular Cloning 1989, CSH:11.47.
Reek et al. Cell 1987, vol. 50:667.
Harper et al. Cell 1993, 75:805–816.
Ngo et al., in:*The Protein Folding Problem and Tertiary Structure Prediction*, 1994, Merz et al., (ed.), Birkhauser, Boston, MA, pp. 433 and 492–495.
Chan, F.K.M. et al. "Identification of Human and Mouse p19, a Novel CDK4 and CDK6 Inhibitor with Homology to p16INK4" *Mol. Cell. Biol.*, vol. 15, pp. 2682–2688.
Guan, K.–L. et al. "Growth Suppression by p18, A p16INK4/MTS1— and p14INK4b/MTS2–Related CDK6 Inhibitor, Correlates with Wild Type pRb Function" *Genes & Development*, vol. 8, pp. 2939–2952.
Hannon, G.J. and Beach, D. "p15INK4B is a Potential Effector of TGF–beta–induced Cell Cycle Arrest" *Nature*, vol. 371, pp. 257–261.
Azzi, L. et al. (1994) "Purification of a 15–kDa cdk4– and cdk5–binding Protein" *Journal of Biological Chemistry*, vol. 269, No. 18, pp. 13279–13288.

Barnard, J.A. et al. (1990) "The cell biology of transforming growth factor β" *Biochimica et Biophysica Acta*, vol. 1032, pp. 79–87.
Bates, S. et al. (1994) "Absence of cyclin D/cdk complexes in cells lacking functional retinoblastoma protein" *Oncogene*, vol. 9, pp. 1633–1640.
Bates, S. et al. (1993) "CDK6 (PLSTIRE) and CDK4 (PSK–J3) are a distinct subset of the cyclin–dependent kinases that associate with cyclin D1" *Oncogene*, vol. 9, pp. 71–79.
Bonetta, L. (1994) "Open questions of p16" *Nature*, vol. 370, p. 180.
Booher, R.N. et al. (1989) "The Fission Yeast cdc2/cdc13/suc1 Protein Kinase: Regulation of Catalytic Activity and Nuclear Localization" *Cell*, vol. 58, pp. 485–497.
Boukamp. P. et al. (1988) "Normal Keratinization in a Spontaneously Immortalized Aneupoloid Human Keratinocyte Cell Line" *Journal of Cell Biology*, vol. 106, pp. 761–771.
Cairns, P. et al. (1994) "Rates of p16 (MTS1) Mutations in Primary Tumors with 9p Loss" *Science*, vol. 265, pp. 415–416.
Caldas, C. et al. (1994) "Frequent somatic mutations and homozygous deletions of the p16 (MTS1) gene in pancreatic adenocarcinoma" *Nature Genetics*, vol. 8, No. 1, pp. 27–32.
Cannon–Albright, L.A. (1992) "Assignment of a Locus for Familial Melanoma, MLM, to Chromosome 9p13–p22" *Science*, vol. 258, pp. 1148–1152.
Cavenee, W.K. et al. (1983) "Expression of recessive alleles by chromosomal mechanisms in retinoblastoma" *Nature*, vol. 305, pp. 779–784.
Cavenee, W.K. et al. (1986) "Prediction of Familial Predisposition to Retinoblastoma" *New England Journal of Medicine*, vol. 314, No. 19, pp. 1201–1207.

(List continued on next page.)

*Primary Examiner*—Bruce R. Campell
*Assistant Examiner*—Dave Trong Nguyen
*Attorney, Agent, or Firm*—Foley, Hoag & Eliot LLP; Matthew P. Vincent; Anita Varma

[57] ABSTRACT

The present invention relates to the discovery in eukaryotic cells, particularly mammalian cells, of a novel family of cell-cycle regulatory proteins ("CCR-proteins"). As described herein, this family of proteins includes a polypeptide having an apparent molecular weight of 16 kDa, and a polypeptide having an apparent molecular weight of approximately 15 kDa, each of which can function as an inhibitor of cell-cycle progression, and therefore ultimately of cell growth. Thus, similar to the role of p21 to the p53 checkpoint, the subject CCR-proteins may function coordinately with the cell-cycle regulatory protein, retinoblastoma (RB). Furthermore, the CCR-protein family includes a protein having an apparent molecular weight of 13.5 kDa (hereinafter "p13.5"). The presumptive role of p13.5, like p16 and p15, is in the regulation of the cell-cycle.

40 Claims, 11 Drawing Sheets

OTHER PUBLICATIONS

Cheng, J.Q. et al. (1993) "Homozygous Deletions within 9p21–p22 Identify a Small Critical Region of Chromosomal Loss in Human Malignant Mesotheliomas" *Cancer Research*, vol. 53, pp. 4761–4763.

Kato, J–Y. et al. (1993) "Direct binding of cyclin D to the retinoblastoma gene product (pRb) and pRb phosphorylation by the cyclin D–dependent kinase CDK4" *Genes & Development*, vol. 7, pp. 331–342.

Knudson, Jr., A.G. (1971) "Mutation and Cancer: Statistical Study of Retinoblastoma" *Proc. Natl. Acad. Sci. USA*, vol. 68, No. 4, pp. 820–823.

Koff, A. et al. (1993) "Negative Regulation of G1 in Mammalian Cells: Inhibition of Cyclin E–Dependent Kinase by TGF–$\beta$" *Science*, vol. 260, pp. 536–538.

Laiho, M. et al. (1990) "Growth Inhibition by TGF–$\beta$ Linked to Suppression of Retinoblastoma Protein Phosphorylation" *Cell*, vol. 62, pp. 175–185.

Lew, D.J. et al. (1991) "Isolation of Three Novel Human Cyclins by Rescue of G1 Cyclin (Cln) Function in Yeast" *Cell*, vol. 66, pp. 1197–1206.

Li, Y. et al. (1994) "Cell cycle expression and p53 regulation of the cyclin–dependent kinase inhibitor p21" *Oncogene*, vol. 9, pp. 2261–2268.

Marcote, M.J. et al. (1993) "A Three–Dimensional Model of the Cdc2 Protein Kinase: Localization of Cyclin– and Suc1–Binding Regions and Phosphorylation Sites" *Molecular and Cellular Biology*, vol. 13, No. 8, pp. 5122–5131.

Marx, J. (1994) "A Challenge to p16 Gene as A Major Tumor Suppressor" *Science*, vol. 264, p. 1846.

Marx, J. (1994) "Link to Hereditary Melanoma Brightens Mood for p16 Gene" *Science*, vol. 265, pp. 1364–1365.

Marx, J. (1994) "New Tumor Suppressor May Rival p53" *Science*, vol. 264, pp. 344–345.

Massagué, J. (1990) "The Transforming Growth Factor–$\beta$ Family" *Annu. Rev. Cell Biol.*, vol. 6, pp. 597–641.

Masui, T. et al. (1986) "Type $\beta$ transforming growth factor is the primary differentiation–inducing serum factor for normal human bronchial epithelial cells" *Proc. Natl. Acad. Sci. USA*, vol. 83, pp. 2438–2442.

Matsushime, H. et al. (1991) "Colony–Stimulating Factor 1 Regulates Novel Cyclins during the G1 Phase of the Cell Cycle" *Cell*, vol. 65, pp. 701–713.

Matsushime, H. et al. (1992) "Identification and Properties of an Atypical Catalytic Subunit (p34$^{PSKJ3}$/cdk4) for Mammalian D Type G1 Cyclins" *Cell*, vol. 71, pp. 323–334.

McKinnon, R.D. et al. (1993) "A Role for TGF–$\beta$ in Oligodendrocyte Differentiation" *Journal of Cell Biology*, vol. 121, No. 6, pp. 1397–1407.

Meyerson, M. and Harlow, E. (1994) "Identification of $G_1$ Kinase Activity for cdk6, a Novel Cyclin D Partner" *Molecular and Cellular Biology*, vol. 14, No. 3, pp. 2077–2086.

Morgan, D.O. and De Bondt, H.L. (1994) "Protein kinase regulation: insights from crystal structure analysis" *Current Opinion in Cell Biology*, vol. 6, pp. 239–246.

Mori, T. et al. (1994) "Frequent Somatic Mutation of the MTSI/CDK4I (Multiple Tumor Suppressor/Cyclin–dependent Kinase 4 Inhibitor) Gene in Esophageal Squamous Cell Carcinoma" *Cancer Research*, vol. 54, pp. 3396–3397.

Motokura, T. et al. (1991) "A novel cyclin encoded by a bcl1–linked candidate oncogene" *Nature*, vol. 350, pp. 512–515.

Mowat, M. et al. (1985) "Rearrangements of the cellular p53 gene in erythroleukaemic cells transformed by Friend virus" *Nature*, vol. 314, pp. 633–636.

Nobori, T. et al. (1994) "Deletions of the cyclin–dependent kinase–4 inhibitor gene in multiple human cancers" *Nature*, vol. 368, pp. 753–756.

Paris, J. et al. (1994) "Study of the higher eukaryotic gene function CDK2 using fission yeast" *Journal of Cell Science*, vol. 107, pp. 615–623.

Parker, C. et al. (1994) "Metastasis–Associated mst1 Gene Expression Correlates with Increased p53 Detection in the B16 Murine Melanoma" *DNA and Cell Biology*, vol. 13, No. 4, pp. 343–351.

Pepose, J.S. and Leib, D.A. (1994) "Recent Breakthroughs in the Molecular Genetics of Ocular Diseases" *Investigative Ophthalmology & Visual Science*, vol. 35, No. 6, pp. 2662–2666.

Pietenpol, J.A. et al. (1990) "TGF–$\beta$ Inhibition of c–myc Transcription and Growth in Keratinocytes Is Abrogated by Viral Transforming Proteins with pRB Binding Domains" *Cell*, vol. 61, pp. 777–785.

Pines, J. and Hunter, T. (1990) "Human cyclin A is adenovirus E1A–associated protein p60 and behaves differntly from cyclin B" *Nature*, vol. 346, pp. 760–763.

Polyak, K. et al. (1994) "p27$^{Kip1}$, a cyclin–Cdk inhibitor, links transforming growth factor–$\beta$ and contact inhibition to cell cycle arrest" *Genes & Development*, vol. 8, pp. 9–22.

Potashkin, J.A. and Beach, D.H. (1988) "Multiple phosphorylated forms of the product of the fission yeast cell division cycle gene cdc2$^+$" *Current Genetics*, vol. 14, pp. 235–240.

Quelle, D.E. et al. (1993) "Overexpression of mouse D–type cyclins accelerates $G_1$ phase in rodent fibroblasts" *Genes & Development*, vol. 7, pp. 1559–1571.

Rodeck, U. et al. (1994) "Transforming Growth Factor $\beta$ Production and Responsiveness in Normal Human Melanocytes and Melanoma Cells" *Cancer Research*, vol. 54, pp. 575–581.

Serrano, M. et al. (1993) "A new regulatory motif in cell–cycle control causing specific inhibition of cyclin D/CDK4" *Nature*, vol. 366, pp. 704–707.

Sherr, C.J. (1993) "Mammalian $G_1$ Cyclins" *Cell*, vol. 73, pp. 1059–1065.

Sporn, M.B. and Roberts, A.B. (1992) "Transforming Growth Factor–$\beta$: Recent Progress and New Challenges" *Journal of Cell Biology*, vol. 119, No. 5, pp. 1017–1021.

Spruck III, C.H. (1994) "p16 gene in uncultured tumours" *Nature*, vol. 370, pp. 183–184.

Tam, S.W. et al. (1994) "Differential expression and regulation of Cyclin D1 protein in normal and tumor human cells: association with Cdk4 is required for Cyclin D1 function in G1 progression" *Oncogene*, vol. 9, pp. 2663–2674.

Toyoshima, H. and Hunter, T. (1994) "p27, a Novel Inhibitor of G1 Cyclin–Cdk Protein Kinase Activity, Is Related to p21" *Cell*, vol. 78, pp. 67–74.

Wainwright, B. (1994) "Familial melanoma and p16 — A hung jury" *Nature Genetics*, vol. 8, No. 1, pp. 3–5.

Walker, G.J. et al. (1994) "Refined localization of the melanoma (MLM) gene on chromosome 9p by anaylsis of allelic deletions" *Oncogene*, vol. 9, pp. 819–824.

Wang, J. et al. (1990) "Hepatitis B virus integration in a cyclin A gene in a hepatocellular carcinoma" *Nature*, vol. 343, pp. 555–557.

Weinberg, R.A. (1988) "Finding the Anti–Oncogene" *Scientific American*, vol. 259, No. 3, pp. 44–51.

Weinberg, R.A. (1991) "Tumor Suppressor Genes" *Science*, vol. 254, pp. 1138–1146.

Xiong, Y. et al. (1992) "D Type Cyclins Associate with Multiple Protein Kinases and the DNA Replication and Repair Factor PCNA" *Cell*, vol. 71, pp. 505–514.

Xiong, Y. et al. (1991) "Human D–Type Cyclin" *Cell*, vol. 65, pp. 691–699.

Xiong, Y. et al. (1992) "Molecular Cloning and Chromosomal Mapping of CCND Genes Encoding Human D–Type Cyclins" *Genomics*, vol. 13, pp. 575–584.

Xiong, Y. et al. (1993) "p21 is a universal inhibitor of cyclin kinases" *Nature*, vol. 366, pp. 701–704.

Xiong, Y. et al. (1993) "Subunit rearrangement of the cyclin–dependent kinases is associated with cellular transformation" *Genes & Development*, vol. 7, pp. 1572–1583.

Zhang, H. et al. (1993) "Proliferating Cell Nuclear Antigen and p21 Are Components of Multiple Cell Cycle Kinase Complexes" *Molecular Biology of the Cell*, vol. 4, pp. 897–906.

```
     Ex12                                    NTp16.2
CGGAGAGGGAATTCGGCACGAGGCAGCATGGAGCCTTCGGCTGACT
                                  Ex1
GGCTGGCCACGGCCGCGGCCCGGGGTCGGGTAGAGGAGGTGCGGGC
                                       Ex13
GCTGCTGGAGGCGGTGGCGCTGCCCAACGCACCGAATAGTTACGGT
   NTp16.3                             Ex14
CGGAGGCCGATCCAGGTCATGGATGATGGGCAGCGCCCGAGTGGC
            Ex2
GGAGCTGCTGCTGCTCCACGGCGCGGAGCCCAACTGCGCCGACCCC
            p16INT
GCCACTCTCACCCGACCCGTGCACCACGCTGCCCGGGAGGGCTTCT
        NTp16.5                                        E
GGACACGCTGGTGGTGCTGCACCGGGCCGGGGCGCGGCTGGACGTG     x
                    Ex3                                o
CGCGATGCCTGGGGCCGTCTGCCCGTGGACCTGGCTGAGGAGCTGG     n

GCCATCGCGATGTCGCACGGTACCTGCGCGCCCGTGCGGGGGGCAC     2
                              Ex15
CAGAGGCAGTAACCATGCCCGCATAGATGCCGCGGAAGGTCCCTCA
   Ex8                     Ex4
GACATCCCCGATTGAAAGAACCAGAGAGGCTCTGAGAAACCTCGGG
         Ex5
AAACTTAGATCATCAGTCACCGAAGGTCCTACAGGGCCACAACTGC

CCCCGCCACAACCCACCCCGCTTTCGTAGTTTTCATTTAGAAAATA

GAGCTTTTAAAAATGTCCTGCCTTTTAACGTAGATATAAGCCTTCC

CCCACTACCGTAAATGTCCATTTATATCATTTTTTATATATTCTTA

TAAAAATGTAAAAAGAAAACACCGCTTCTGCCTTTTCACTGTGTT
```

*Figure 1A*

```
                    Ex6
        _____↘
GGAGTTTTCTGGAGTGAGCACTCACGCCCTAAGCGCACATTCATGT

GGGCATTTCTTGCGAGCCTCGCAGCCTCCGGAAGCTGTCGACTTCA
             ↙        Ex7
TGACAAGCATTTTGTGAACTAGGGAAGCTCAGGGGGGTTACTGGCT

TCTCTTGAGTCACACTGCTAGCAAATGGCAGAACCAAAGCTCAAAT

AAAAATAAAATTATTTTCATTCATTCACTCAAAAAAA
```

*Figure 1B*

```
p16ex1    <  GGNGGNAAGNTGTGGGGGAAAGTTTGGGGATGGAANACCAANCCCTCCTTTCNTTACCAA

.........+.........+.........+.........+.........+.........+ p16ex1    <  ACNCTGGCTCTGNCGAGGCTNCNTCCGANTGGTNCCCCCGGGGGAGACCCAACCTGGGNC
p16ex1    <  GACTTCAGGGNTGCNACATTCACTAAGTGCTNGGAGNTAATANCACCTCCTCCGAGCANx
p16ex13                              TCNCTTATTGNTAGGANATAATAACACCTCCACCGATAACT

.........+.........+.........+.........+.........+.........+ p16ex1    <  TCGCTCACAGCGTCCCCTTACCTNGANAGATACCNCGXGXTCCCTCCAGAGGATTTGAGG
p16ex13   <  TCACTTACAACGTCCCNNTTCCTGGAAAGATACACAGCGTTCCCTCCAGAGGATTTGTGG

.........+.........+.........+.........+.........+.........+ p16ex1    <  GACAGGNTCGGAGGGGGCTCTTCCCCCANCACCGGAGGAAGAAAGAGGAGGGNCTGACTG
p16ex13   <  GACAGGGTNGGAGNGGTCTCTTCCNCCACCACCGGAGGAAGAAAGAGGAGGGGCTGNCTG

.........+.........+.........+.........+.........+.........+
                                                      -----Ex1A--(12)-->
p16ex1    <  GTCACCAGAGGGTGGGACGGACCGCGTGCGCTCGGCGNCTNCGGAGAGGGGGAGAACAGA
p16ex13   <  TTCACCAGAGGGTGGGACGGACCNCGTACGCTCGNCGNCTNCGGAGAGGGGGAGAGCAGT

.........+.........+.........+.........+.........+.........+ p16ex1    <  CAACGGGCGGCGGGGAGCAGCATGGATCCGGCGGCGGGGAGCAGCATGGANCCTTCGACT
p16ex13   <  CANCGGNCGNCGGGGAGCAACATGGAACCGNCGGCGGGGAGCAGCATGGANCCTTCGGCT

.........+.........+.........+.........+.........+.........+ p16NT2    <              GACNNNCTCCGGCCGGNGTCGGGTAGAGGAGGTGCGGGCGCTGCTGGAG
p16ex1    <  GACTGACTGCCTCGC
p16ex13   <  GACTGGCTGNCCACGNCCACGNCCCGGGGTCGGGTAGAGGAGGTGCGGNCGCTNCTGGAG

.........+.........+.........+.........+.........+.........+
                          <---------Ex13----------
p16nt3    >                                               CTCTNANCCCGGGTA
p16nt2    <  GCGGGGGCGCTGCCCAACGCACCGAATAGTTACGGTCGGAGGCCGATCCAGGTXXGGGTA
p16ex13   <  GCGGGGNCTCTGNCCAACNCGCTAAAAN

.........+.........+.........+.........+.........+.........+ p16nt3    >  GAGGGTCTGCAGCGGGAGCAGNGGATGGCGGGCGACTCTGGAGGACGAAGTTGGCAGGGG
p16nt2    <  GAGGGTCTGCAGCGGGAGCAGGGGATGGCGGGCGACTCTGGAGGACGAAGTTTGCAGGGG

.........+.........+.........+.........+.........+.........+
                                      <----------Ex1B------
p16nt3    >  AATTGGAATCAGGTAGCGCTTCGANTCTCCGGAAAAAGGGGAGGCTTCCTGGGGAGTTNN
p16nt2    <  AATTGGAATCAGGTAGCGCTTCGATTCTCCNGAAAAAGGGGAGGCTTCCTGGGGAGTTTT
```

*Figure 2A*

```
            .........+.........+.........+.........+.........+.........+
p16nt3    > CAGAAGGGGTTTGTAATCACAGNCCTCCNCCTGGCGACGCCCTGGGGGGTTGGGAAGCCA
p16nt2    < CAGAAGGGGTTTGTAATCACAGACCTCCTCCTGGCGACGTCCTGGGGGCTTGGGAAGCCA

.........+.........+.........+.........+.........+.........+
p16nt3    > AGGAAGAGGAATGAGGAGNCACGCGCNTACAGNTCTCTCGAATNCTGANAAGATCTGAAG
p16nt2    < AGGAAGAGGAATNAGGAGCCACGCGCGTACAGATCTCTCGAATGCTGAGAAGATCTNAAG

.........+.........+.........+.........+.........+.........+
p16nt3    > GGGGGAACATATTTGTATTAGxATNNAAGTATGCTCTTTATCAGATACAAAATTCACGAA
p16nt2    < GGGGGAACATATTTGTATTAGCNTCCAAGTNTNCTCTNTATCANATACAAANTxC

.........+.........+.........+.........+.........+.........+
p16nt3    > CGTGTGGNATAAAAAGGGAGTCTTAAAGAAATNTAAGATGTGCTGGGACTACTTAGCCTC
p16nt3    > CAANACACAGATNCCTGGATGGAGCT
```

*Figure 2B*

```
p16int  >  AAAANNAAAAAAAATCTCCCAGGCCTAACATAATTNTCAGGAAAGAAATTTCAGTAGTTG
           .........+.........+.........+.........+.........+.........+ p16int  >  NATCTCAGGGGAAATACAGGAAGTTAGCCTGGAGTAAAAGTCAGTCTGTCCCTGCCCCTT
           .........+.........+.........+.........+.........+.........+ p16int  >  TGCTANATTGCCCGTGCCTCACAGTGCTCTCTGCCTGTGACGACAGCTCCNCAGAAGTTC
           .........+.........+.........+.........+.........+.........+ p16int  >  GGAGGATATAATGGAATTCATTGTGTACTGAAGAATGGATAGAGAACTCAAGAAGGAAAT
           .........+.........+.........+.........+.........+.........+ p16int  >  TGGAAACTGGAAGCAAATGTAGGGGTAATTAGACACCTGGGGCTTGTGTGGGGTCTGCT
p16ex15 <                                      AANAAAAAAGAAATNGATAANATAGAGGAT
           .........+.........+.........+.........+.........+.........+

----------EX2A------->
p16int  >  TGGCGGTGAGGGGGCTCTACACAAGCTTCCTTTCCGTCATGCCGNCCCCCACCCTGGCTC
p16ex15 <  GAACANATTAAAATCAAAAAACANAACANAGACATAATAAAAAACGAGAATGTTCTAGAC
           .........+.........+.........+.........+.........+.........+

------EX14-------
p16int  >  TGACCATTCTGTTCTCTCTGGCAGGTCATGATGATGGGCAGCGCCCGAGTGGCGGAGCTG
p16ex15 <  NTAATCATAATTATAAAGGTCAAGACTCATTGATATnAAGGAAATTGAAGGGAAATCTTA
           .........+.........+.........+.........+.........+.........+

->
p16int  >  CTGCTGCTCCACGGCGCGGAGCCCAACTGCTCCGACGCCG
p16ex2  >                              CCTGCNACGACCCCGCCACTCTCACCCGACCCGTG
p16ex14 >             NCTCTCACGGTGGGGAGGCCAACTGCGCCGAACCCGCCACTCTCACCCGACCCGCG
p16ex15 <  ACTAGCACAANNGNATNAAAAAANAATTCCCACGACACCGCCACTCTCAACGCATCCGTG
           .........+.........+.........+.........+.........+.........+ p16ex2  >  CACGACGCTGTCCGGGAGGGTTTCCTGGACACGCTGGTGGTGCTGCACCGGGCCGGGGNG
p16ex14 >  CACGACGGTGCCCGGGAGGGGTTCCTGGACACGCTGGTGGTGCTGCACCGGGCCGGGGCG
p16ex15 <  CTCGACACTGCCCGGGAGGTCNTCCTGGACACGCTGGTGGTNCTCCACCGGNCCGGGGCA
           .........+.........+.........+.........+.........+.........+ p16ex2  >  CGGTTGGACGTGCGCGATGCCTGGGGCCGCCTNCCCGTGGXACCTGGTTGAGGAGCTGGG
p16ex14 >  CGGCTGGACGTTCGNGATGCCTGGGGGCNTCTNTCCGTNGXACCTGGCTGAAGAGCTGGN
p16ex15 <  CGTCTGGACGTGCGCGATGCCTGGGNCCGNCTACCCGTGGTACCTGACTGAGGACCTGGG
           .........+.........+.........+.........+.........+.........+ p16ex2  >  NCATCGCGATGTCGCACGGTACCTGCGCGCGGTTGCGGGGGGCACCAGAGGXNAGTNACC
p16ex14 >  NCATCGNGATGTCGCACGGCCNTGTGTGNGGNTGCGGGGGGCACCATAGGTCAGTNTCC
p16ex15 <  CCATCCCGATTTCGCNGGGTANCTGNGNGNGGCTGNGGGGGCCAANAGAGGXCANTACCC
```

*Figure 2C*

```
P16EX5  < XAAGTATGAGCGAAACNAATTGTGGTTTGAGAANAGGNAATCGTAGGGAACTTCGGGATC
           .........+.........+.........+.........+.........+.........+

P16EX5  < CCNCNGGGANCNCCAGAACCTGAGNCGCCNATTGGAAATNACAAACTGNCTGNATCACTC
           .........+.........+.........+.........+.........+.........+

P16EX5  < CGNACCAGGTNCAAAAGATACCTGGGGANGCGGGAAGGGAAAGACNACATCNAGACCGCC
P16EX9  <                                                         CCCC
           .........+.........+.........+.........+.........+.........+

P16EX5  < TTCGCNCCTXGGNATTGTGAGCAGCCTCTGAGACTCATTXATATNACACTCGTXTTTCTT
P16EX9  < ATCGCGCCTTGGGANTGTGAGCNACCATTGAGACTCATNAATATAGCACTCGTTTTTCTT
           .........+.........+.........+.........+.........+.........+

P16EX5  < CTTACAACCCTGCGGNCCGCGCGGTCGCGCTTTCTCTGCCCTCCGCCGGGTGGACCTGGA
P16EX9  < CTTGCAACCCTGCGGNCCGCGCGGTCGCGCTNTCTCTGCCCTCCGCNGGGTGGACCTGGA
           .........+.........+.........+.........+.........+.........+

P16EX5  < GCGCTTGAGCGGTCGGCGCGCCTGGAGCAGCCAGGCGGNCAGTGGACTAGCTGCTGGACC
P16EX9  < GCGCTTGAGCGGTCGGCGCNCCTGGANCAGCCAGGCGGGCAGTGGACTACCTNCTGGACC
           .........+.........+.........+.........+.........+.........+

P16EX5  < AGGGAGGTGTGGGAGAGCGGTGGCGGCGGGTACATGCACGTGAAGCCATTGCGAGAACTT
P16EX9  < AGGGAGGTGTGGGAGAGCGGTGNCGGCGGGTACATGCACGTGAAGCCATTGCGAGAACTT
           .........+.........+.........+.........+.........+.........+

P16EX5  < TATCCATAAGTATTTCAATACCGGTAGGGACGGCAAGAGAGGAGGGCGGGATGTGCCACA
P16EX5  < TATCCATAAGTATTTCAATGCCGGTAGGGACGGCAAGAGAGGAGGGCGGGATGTNCCACA
           .........+.........+.........+.........+.........+.........+

P16EX5  < CATCTTTGACCTCAGGTTTCTAACGCCTGTTTTCTTTCTGCCCTCTGCAGACAACCCCGA
P16EX9  < CATCTTTGACCTCAGGTTTCTAACGCCTGTTTTCTTTCTGCCCTCTGCAGACATCCCCGA
           .........+.........+.........+.........+.........+.........+

P16EX4  >                                     AGAAATTAGATCATCAGTCACCGATG
P16EX5  < TTGAAAGAACCAGAGAGGCTCTGAGAAACC
P16EX9  < TTGAAAGAACCAGAGAGGCTCTGAGAAACCTCCGGAAACTTAGXTCATCAXTCGCCGNAA
           .........+.........+.........+.........+.........+.........+

P16EX4  > GTCCTACAGGGNCACAACTGNCCCCGCCACAACCCACCCCGNTTTCGTAGTTTTCATTTA
P16EX9  < AA
```

*Figure 3A*

```
P16EX4   > GAAAATAGAGCTTTTAAAAATGTCCTGCCTTTTAACGTAGATATATGCCTTCCCCCACTA
           .........+.........+.........+.........+.........+.........+

P16EX4   > CCGNAAATGTCCATTTATATCATNTTTTATATATTCTTATAAAAATGTAAAAAAGAAAAA
           .........+.........+.........+.........+.........+.........+

P16EX4   > CACCGCTTCTGCCTTTTCACTGTGTTGGAGTTTTCTGGAGTGAGCACTCACGCCCTAAGC
           .........+.........+.........+.........+.........+.........+

P16EX6   >    CANCNATNTNCGGCATTTCTNGNGAGCCTCGTAGTCTCCGGATGNTGTCGACCTCGAG
P16EX6A  >    CANCNATNTNCGGCATTTCTNGNGAGCCTCGTAGTCTCCGGATGNTGTCGACCTCGAG
P16EX4   > GCACATTCATGTGGGCATTTCTTGCGAGCCTCGCAGNCTCCGGAAGCTGTCGACCTCGAG
           .........+.........+.........+.........+.........+.........+

P16EX6   > GGGGGGNCCNGTACCCAATTCGNCCTATNGTGAGTCGTNTTACAATTCACTGGCCGCCGT
P16EX6A  > GGGGGGNCCNGTACCCAATTCGNCCTATNGTGAGTCGTNTTACAATTCACTGGCCGCCGT
P16EX4   > GGGGGGNCCGGTACCCAATTCGCCCTATAGTGAGTCGTATTACAATTCACTGGNCGNCGN
           .........+.........+.........+.........+.........+.........+

P16EX6   > TTTXACAACGTCGXTGXACTGGGAAAACCCTGGTGTTACCCAACTTXAATCGCCTTGNAG
P16EX6A  > TTTXACAACGTCGXTGXACTGGGAAAACCCTGGTGTTACCCAACTTXAATCGCCTTGNAG
P16EX4   > TTTTACAACGTCGGTGGACTGGGAAAACCCCGGNGTTACCCAACTTTAATCGNCTTGGAG
           .........+.........+.........+.........+.........+.........+

P16EX6   > NACATCCCCCTTTXCGCCAGCTGGTGTAATAGCGANGAGGCCCGCACCGATCGCCCTTCC
P16EX6A  > NACATCCCCCTTTXCGCCAGCTGGTGTAATAGCGANGAGGCCCGCACCGATCGCCCTTCC
P16EX4   > GACATCCCCCTTTTCGCCAGNTGGGGTTATAGNGAAGAGGGCCNCACCNNTCGCCC
           .........+.........+.........+.........+.........+.........+

P16EX6   > CAACAGTTGNGCAGCCTGAATGGCGAATGGAAATTGTAAGCGTTAATATTTTGTTAAAAT
P16EX6A  > CAACAGTTGNGCAGCCTGAATGGCGAATGGAAATTGTAAGCGTTAATATTTTGTTAAAAT
           .........+.........+.........+.........+.........+.........+

P16EX6   > TCGCGTTANATCNTCGGTTAANTCAGCTCATNTTTTATCCAATAGGCCGANATCGGCANA
P16EX6A  > TCGCGTTANATCNTCGGTTAANTCAGCTCATNTTTTATCCAATAGGCCGANATCGGCANA
           .........+.........+.........+.........+.........+.........+

P16EX6   > ATCCCCAATAAATCAANAGAATAGACCGAGATAGGGTTGAGTGTCGTTCCAGTTNGGGAA
P16EX6A  > ATCCCCAATAAATCAANAGAATAGACCGAGATAGGGTTGAGTGTCGTTCCAGTTNGGGAA
           .........+.........+.........+.........+.........+.........+

P16EX6   > CANGAGTCCACTATTAAAGANCGTAGNCTCNAACGTCANAGGGCGAAAAACCNTNTTTCA
P16EX6A  > CANGAGTCCACTATTAAAGANCGTAGNCTCNAACGTCANAGGGCGAAAAACCNTNTTTCA
```

P16EX6  > GNGGATTGGNCCACTACGCNTANCC
P16EX6A > GNGGATTGGNCCACTACGCNTANCCATCACCCTATTC
```

| cell | H9 | U18 | CCL119 | MCF-7 | HTB 125 | SaOs2 | A431 | normal #1 | normal #2 |
|---|---|---|---|---|---|---|---|---|---|
| exon 1 | absent | absent | absent | absent | absent | altered | altered | norm | norm |
| exon 2 | absent | absent | absent | absent | absent | altered | absent | norm | norm |

| cell | WI38 | CCL120 | HeLa | HTB100 | ZRB75 | GM130 | Tera2 | HTB172 | HTB173 |
|---|---|---|---|---|---|---|---|---|---|
| exon 1 | norm | norm | norm | norm | norm | norm | norm | norm | norm |
| exon 2 | norm | norm | norm | norm | norm | norm | norm | norm | norm |

Figure 6

```
p16: Ile Gln Val Met Met Met Gly Ser Ala Arg Val Ala Glu Leu Leu Leu His Gly Ala Glu Pro Asn
p15: Ile Gln Val Met Met Met Gly Ser Ala Arg Val Ala Glu Leu Leu Leu His Gly Ala Glu Pro Asn
p13:                 Met Met Met Gly Asn Val His Val Ala Ala Leu Leu Leu Asn Tyr Gly Ala Asp Ser Asn

Cys Ala Asp Pro Ala Thr Leu  *  Thr Arg Pro Val His Asp Ala Ala Arg Glu Gly Phe Leu Asp Thr
Cys Ala Asp Pro Ala Thr Leu  *  Thr Arg Pro Val His Asp Ala Ala Arg Glu Gly Phe Leu Asp Thr
Cys Glu Asp Pro  *  Thr Thr Phe Ser Arg Pro Val His Asp Ala Ala Arg Glu Gly Phe Leu Asp Thr

Leu Val Val Leu His Arg Ala Gly Ala Arg Leu Asp Val Arg Asp Ala Trp Gly Arg Leu Pro Val Asp
Leu Val Val Leu His Arg Ala Gly Ala Arg Leu Asp Val Arg Asp Ala Trp Gly Arg Leu Pro Val Asp
Leu Val Val Leu His Gly Ser Gly Ala Arg Leu Asp Val Arg Asp Ala Trp Gly Arg Leu Pro Leu Asp

Leu Ala Glu Glu Leu Gly His Arg Asp Val Ala Arg Tyr Leu Arg Ala Ala Ala Gly Gly Thr . . . . .
Leu Ala Glu Glu Leu Gly Arg Gly His Arg Asp Val Ala Gly Tyr Leu Arg Thr Ala Thr Gly Asp
Leu Ala Gln Glu Arg Gly His Gln Asp Ile Val Arg Tyr Leu Arg Ser Ala  *  Gly Cys Ser . . . . .
```

CELL-CYCLE REGULATORY PROTEINS, AND USES RELATED THERETO

RELATED APPLICATIONS

This application is a continuation-in-part of U.S. Ser. No. 08/248,812 filed May 25, 1994 and entitled "Cell-cycle Regulatory Protein, and Uses Related Thereto", which is a continuation-in-part of U.S. Ser. No. 08/227,371 filed Apr. 14, 1994 and entitled "Cell-cycle Regulatory Protein, and Uses Related Thereto", which is a continuation-in-part of U.S. Ser. No. 08/154,915 filed Nov. 18, 1993 and entitled "Cyclin Complex Rearrangements and Uses Related Thereto", which is a continuation-in-part of U.S. Ser. No. 07/991,997 filed Dec. 17, 1992 and entitled "Cyclin Complex Rearrangements and Uses Related Thereto", now abandoned, which is a continuation-in-part of U.S. Ser. No. 07/963,308 filed Oct. 16, 1992 and entitled "D-Type Cyclin and Uses Related Thereto". The teachings of U.S. Ser. Nos. 08/248,812, 08/227,371, 08/154,915, 07/991,997, 07/963, 308 and related PCT publication US 93/09945 are incorporated herein by reference.

FUNDING

Work described herein was supported by National Institutes under NIH Grant Nos. RO1 GM39620 and R01 CA63518 of Health Grant and the Howard Hughes Medical Institute. The United States Government has certain rights in the invention.

BACKGROUND OF THE INVENTION

Neoplasia is characterized by deregulated cell growth and division. Inevitably, molecular pathways controlling cell growth must interact with those regulating cell division. It was not until very recently, however, that experimental evidence became available to bring such connection to light. Cyclin A was found in association with the adenovirus oncoprotein E1A in virally transformed cells (Giordona et al. *Cell* 58:981 (1989); and Pines et al. *Nature* 346:760 (1990)). In an early hepatocellular carcinoma, the human cyclin A gene was found to be the integration site of a fragment of the hepatitis B virus, which leads to activation of cyclin A transcription and a chimeric viral cyclin A protein that is not degradable in vitro (Wang et al. *Nature* 3 3:555 (1990)). The cell-cycle gene implicated most strongly in oncogenesis thus far is the human cyclin D1. It was originally isolated through genetic complementation of yeast $G_1$ cyclin deficient strains (Xiong et al. *Cell* 65:691 (1991); and Lew et al. *Cell* 66:1197 (1991)), as cellular genes whose transcription is stimulated by CSF-1 in murine macrophages (Matsushine et al. *Cell* 65:701 (1991)) and in the putative oncogene PRAD1 rearranged in parathyroid tumors (Montokura et al. *Nature* 350:512 (1991). Two additional human D-type cyclins, cyclins D2 and D3, were subsequently identified using PCR and low-stringency hybridiazation techniques (Inaba et al. *Genomics* 13:565 (1992); and Xiong et al. *Genomics* 13:575 (1992)). Cyclin D1 is genetically linked to the bcl-1 oncogene, a locus activated by translocation to an immunoglobulin gene enhancer in some B-cell lymphomas and leukemias, and located at a site of gene amplification in 15–20% of human breast cancers and 25–48% of squamous cell cancers of head and neck origin.

However, the creation of a mutant onocogene is only one of the requirements needed for tumor formation; tumorigenesis appears to also require the additional inactivation of a second class of critical genes: the "anti-oncogenes" or "tumor-suppressing genes." In their natural state these genes act to suppress cell proliferation. Damage to such genes leads to a loss of this suppression, and thereby results in tumorigenesis. Thus, the deregulation of cell growth may be mediated by either the activation of oncogenes or the inactivation of tumor-suppressing genes (Weinberg, R. A., (September 1988) *Scientific Amer.* pp 44–51).

Oncogenes and tumor-suppressing genes have a basic distinguished feature. The oncogenes identified thus far have arisen only in somatic cells, and thus have been incapable of transmitting their effects to the germ line of the host animal. In contrast, mutations in tumor-suppressing genes can be identified in germ line cells, and are thus transmissible to an animal's progeny.

The classic example of a hereditary cancer is retinoblastomas in children. The incidence of the retinoblastomas is determined by a tumor suppressor gene, the retinoblastoma (RB) gene (Weinberg, R. A., (September 1988) *Scientific Amer.* pp 44–51; Hansen et al. (1988) *Trends Genet* 4:125–128). Individuals born with a lesion in one of the RB alleles are predisposed to early childhood development of retinoblastomas. Inactivation or mutation of the second RB allele in one of the somatic cells of these susceptible individuals appears to be the molecular event that leads to tumor formation (Caveneee et al. (1983) *Nature* 305:799–784; Friend et al. (1987) *PNAS* 84:9059–9063).

The RB tumor-suppressing gene has been localized onto human chromosome 13. The mutation may be readily transmitted through the germ line of afflicted individuals (Cavenee, et al. (1986) *New Engl. J. Med* 314:1201–1207). Individuals who have mutations in only one of the two naturally present alleles of this tumor-suppressing gene are predisposed to retinoblastoma. Inactivation of the second of the two alleles is, however, required for tumorigenesis (Knudson (1971) *PNAS* 68:820–823).

A second tumor-suppressing gene is the p53 gene (Green (1989) *Cell* 56:1–3; Mowat et al (1985 *Nature* 314:633–636). The protein encoded by the p53 gene is a nuclear protein that forms a stable complex with both the SV40 large T antigen and the adenovirus E1B 55 kd protein. The p53 gene product may be inactivated by binding to these proteins.

Based on cause and effect analysis of p53 mutants, the fictional role of p53 as a "cell-cycle checkpoint", particularly with respect to controlling progression of a cell from G1 phase into S phase, has implicated p53 as able to directly or indirectly affect cycle cyle machinery. The first firm evidence for a specific biochemical link between p53 and the cell-cycle comes a finding that p53 apparently regulates expression of a second protein, p21, which inhibits cyclin-dependent kinases (CDKs) needed to drive cells through the cell-cycle, e.g. from G1 into S phase. For example, it has been demonstrated that non-viral transformation, such as resulting at least in part from a mutation of deletion of of the p53 tumor suppressor, can result in loss of p21 from cyclin/ CDK complexes. As described Xiong et al. (1993) *Nature* 366:701–704, induction of p21 in response to p53 represents a plausible mechanism for effecting cell-cycle arrest in response to DNA damage, and loss of p53 may deregulate growth by loss of the p21 cell-cycle inhibitor.

The role of RB as a tumor-suppressor protein in cell-cycle control is believed to be similar to that of p53. However, whereas p53 is generally believed to be responsive to such indigenous environmental cues as DNA damage, the RB protein is apparently involved in coordinating cell growth with exogenous stimulus that normally persuade a cell to cease proliferating, such as diffusible growth inhibitors. In normal cells, RB is expressed throughout the cell cycle but exists in multiple phosphorylated forms that are specific for certain phases of the cycle. The more highly phosphorylated forms are found during S and $G_2$/M, whereas the under-phosphorylated forms are the primary species seen in $G_1$ and in the growth arrested state. Base on these observations, it has been argued that if RB is to have a regulatory (suppressive) activity in the cell-cycle, this activity must be regulated at the post-translational level. Accordingly, under-phosphorylated RB would be the form with growth-suppressive activity, since this form is prevalent in G1 and growth arrested cells.

To this end, it is noted that various paracrine growth inhibitors, such as members of the TGF-β family, prevent phosphorylation of RB and arrest cells in late $G_1$. Current models suggest that during G1, cyclin dependent kinases and particularly cyclin D-associated kinases, CDK4 and CDK6, phosphorylate the product of the retinoblastoma susceptibility gene, RB, and thus release cells from its growth inhibitory eflects. TGF-β treatment causes accumulation of RB in the under-phosphorylated state and expression of RB-inactivating viral oncoproteins prevent TGF-β induced cell cycle arrest. In similar fashion, other related differentiation factors, such as activin, induce accumulation of unphosphorylated RB that is correlated with arrest in $G_1$ phase.

Recently, it has been demonstrated that the RB protein is a phosphorylation substrate for both CDK4 and CDK6 (Serano et al. (1993) *Nature* 366:704–707; Kato et al. (1993) *Genes Dev* 7:331–342; and Meyerson et al. (1994) *Mol Cell Biol* 14:2077–2086). However, prior to the present discovery, there was little information concerning the manner by which CDK phosphorylation of RB was negatively regulated.

SUMMARY OF THE INVENTION

The present invention relates to the discovery in eukaryotic cells, particularly mammalian cells, of a novel family of cell-cycle regulatory proteins ("CCR-proteins"). As described herein, this family of proteins includes a polypeptide having an apparent molecular weight of 16 kDa, and a polypeptide having an apparent molecular weight of approximately 15 kDa, each of which can function as an inhibitor of cell-cycle progression, and therefore ultimately of cell growth. Thus, similar to the role of p21 to the p53 checkpoint, the subject CCR-proteins may function coordinately with the cell-cycle regulatory protein, retinoblastoma (RB). Furthermore, the CCR-protein family includes a protein having an apparent molecular weight of 13.5 kDa (hereinafter "p13.5"). The presumptive role of p13.5, like p16 and p15, is in the regulation of the cell-cycle.

One aspect of the invention features a substantially pure preparation of a cell cycle regulatory (CCR) protein, or a fragment thereof, the full-length form of the CCR-protein having an approximate molecular weight in the range of 13 to 16.5 kD, preferably 14.5 kD to 16 kD. In preferred embodiments, the full length form of the CCR-protein has an apparent molecular weight of approximately 13.5 kD, 15 kD, 15.5 kD or 16 kD. In a preferred embodiment: the polypeptide has an amino acid sequence at least 60% homologous to the amino acid sequence represented in one of SEQ ID No. 2, 4 or 6; the polypeptide has an amino acid sequence at least 80% homologous to the amino acid sequence represented in one of SEQ ID No. 2, 4 or 6; the polypeptide has an amino acid sequence at least 90% homologous to the amino acid sequence represented in one of SEQ ID No. 2, 4 or 6; the polypeptide has an amino acid sequence identical to the amino acid sequence represented in one of SEQ ID No. 2, 4 or 6. In a preferred embodiment: the fragment comprises at least 5 contiguous amino acid residues of SEQ ID No. 2, 4 or 6; the fragment comprises at least 20 contiguous amino acid residues of SEQ ID No. 2, 4 or 6; the fragment comprises at least 50 contiguous amino acid residues of SEQ ID No. 2, 4 or 6. For instance, the CCR-protein can comprise an amino acid sequence represented by the general formula:

Met-Met-Met-Gly-Xaa-Xaa-Xaa-Val-Ala-Xaa-Leu-Leu-Leu-Xaa-Xaa- (SEQ ID NO:11)
Gly-Ala-Xaa-Xaa-Asn-Cys-Xaa-Asp-Pro-Xaa-Thr-Xaa-Xaa-Xaa-Arg-
Pro-Val-His-Asp-Ala-Ala-Arg-Glu-Gly-Phe-Leu-Asp-Thr-Leu-Val-
Val-Leu-His-Xaa-Xaa-Gly-Ala-Arg-Leu-Asp-Val-Arg-Asp-Ala-Trp-
Gly-Arg-Leu-Pro-Xaa-Asp-Leu-Ala-Xaa-Glu-Xaa-Gly-His-Xaa-Asp-
Xaa-Xaa-Xaa-Tyr-Leu-Arg-Xaa-Ala-Xaa-Gly

For example, the CCR-protein can be represented by the sequence:

Met-Asp-Pro-Ala-Ala-Gly-Ser-Ser-Met-Glu-Pro-Ser-Ala-Asp-Trp-Leu- (SEQ ID NO:12)
Ala-Thr-Ala-Ala-Ala-Arg-Gly-Arg-Val-Glu-Glu-Val-Arg-Ala-Leu-Leu-
Glu-Ala-Val-Ala-Leu-Pro-Asn-Ala-Pro-Asn-Ser-Tyr-Gly-Arg-Arg-Pro-
Ile-Gln-Val-Met-Met-Met-Gly-Xaa-Xaa-Xaa-Val-Ala-Xaa-Leu-Leu-Leu-
Xaa-Xaa-Gly-Ala-Xaa-Xaa-Asn-Cys-Xaa-Asp-Pro-Xaa-Thr-Xaa-Xaa-Xaa-
Arg-Pro-Val-His-Asp-Ala-Ala-Arg-Glu-Gly-Phe-Leu-Asp-Thr-Leu-Val-
Val-Leu-His-Xaa-Xaa-Gly-Ala-Arg-Leu-Asp-Val-Arg-Asp-Ala-Trp-Gly-
Arg-Leu-Pro-Xaa-Asp-Leu-Ala-Xaa-Glu-Xaa-Gly-His-Xaa-Asp-Xaa-Xaa-
Xaa-Tyr-Leu-Arg-Xaa-Ala-Xaa-Gly-Gly-Thr-Arg-Gly-Ser-Asn-His-Ala-
Arg-Ile-Asp-Ala-Ala-Glu-Gly-Pro-Ser-Asp-Ile-Pro-Asp;

or alternatively, by the sequence:

Met-Arg-Glu-Glu-Asn-Lys-Gly-Met-Pro-Ser-Gly-Gly-Gly-Ser-Asp-Glu- (SEQ ID NO:13)
Gly-Leu-Ala-Thr-Pro-Ala-Arg-Gly-Leu-Val-Glu-Lys-Val-Arg-His-Ser-
Trp-Glu-Ala-Gly-Ala-Asp-Pro-Asn-Gly-Val-Asn-Arg-Phe-Gly-Arg-Arg-
Ala-Ile-Gln-Val-Met-Met-Met-Gly-Xaa-Xaa-Xaa-Val-Ala-Xaa-Leu-Leu-
Leu-Xaa-Xaa-Gly-Ala-Xaa-Xaa-Asn-Cys-Xaa-Asp-Pro-Xaa-Thr-Xaa-Xaa-
Xaa-Arg-Pro-Val-His-Asp-Ala-Ala-Arg-Glu-Gly-Phe-Leu-Asp-Thr-Leu-
Val-Val-Leu-His-Xaa-Xaa-Gly-Ala-Arg-Leu-Asp-Val-Arg-Asp-Ala-Trp-
Gly-Arg-Leu-Pro-Xaa-Asp-Leu-Ala-Xaa-Glu-Xaa-Gly-His-Xaa-Asp-Xaa-
Xaa-Xaa-Tyr-Leu-Arg-Xaa-Ala-Xaa-Gly-Asp, or yet in another embodiment, by the sequence:

Met-Met-Met-Gly-Xaa-Xaa-Xaa-Val-Ala-Xaa-Leu-Leu-Leu-Xaa-Xaa-Gly- (SEQ ID NO:14)
Ala-Xaa-Xaa-Asn-Cys-Xaa-Asp-Pro-Xaa-Thr-Xaa-Xaa-Xaa-Arg-Pro-Val-
His-Asp-Ala-Ala-Arg-Glu-Gly-Phe-Leu-Asp-Thr-Leu-Val-Val-Leu-His-
Xaa-Xaa-Gly-Ala-Arg-Leu-Asp-Val-Arg-Asp-Ala-Trp-Gly-Arg-Leu-Pro-
Xaa-Asp-Leu-Ala-Xaa-Glu-Xaa-Gly-His-Xaa-Asp-Xaa-Xaa-Xaa-Tyr-Leu-
Arg-Xaa-Ala-Xaa-Gly-Cys-Ser-Leu-Cys-Ser-Ala-Gly-Trp-Ser-Leu-Cys-
Thr-Ala-Gly-Asn-Val-Ala-Gln-Thr-Asp-Gly-His-Ser-Phe-Ser-Ser-Ser-
Thr-Pro-Arg-Ala-Leu-Glu-Leu-Arg-Gly-Gln-Ser-Gln-Glu-Gln-Ser.

In preferred embodiments, the CCR-protein specifically binds a CDK, e.g. a $G_1$ phase CDK, e.g. CDK4 and/or CDK6. The CCR-protein can be cloned from a mammalian cell, e.g. a human cell, e.g. a mouse cell.

Another aspect of the present invention features a polypeptide, of the CCR-protein family, which functions in one of either role of an agonist of cell-cycle regulation or an antagonist of cell-cycle regulation. In a preferred embodiment: the subject CCR-protein specifically binds a cyclin dependent kinase (CDK), e.g. specifically binds CDK4; e.g. specifically binds CDK6; e.g. inhibits a kinase acitivity of CDK4; inhibits a kinase acitivity of CDK6; e.g. inhibits phosphorylation of an RB protein by CDK4. In a more preferred embodiment: the CCR-protein regulates a eukaryotic cell-cycle, e.g. a mammalian cell-cycle, e.g., a human cell-cycle; the CCR-protein inhibits proliferation/cell growth of a eukaryotic cell, e.g., a human cell; the CCR-protein inhibits progression of a eukaryotic cell from G1 phase into S phase, e.g., inhibits progression of a mammalian cell from G1 phase into S phase, e.g., inhibits progression of a human cell from G1 phase into S phase; the CCR-protein inhibits the kinase activity of a cyclin dependent kinase (CDK), e.g. a CDK active in G1 phase, e.g. CDK4; the CCR-protein suppresses tumor growth, e.g. in a tumor cell, e.g. in a tumor cell having an unimpaired RB or RB-like protein checkpoint. Moreover, CCR-proteins of the present invention may also have biological activities which include: an ability to regulate cell-cycle progression in response to extracellular factors and cytokines, e.g. functional in paracrine or autocrine regulation of cell growth and/or differentiation, e.g. inhibit CDK activation in response to transforming growth factor-β (TGF-β) or related growth, differentiation or morphogenesis factor.

Yet another aspect of the present invention concerns an immunogen comprising a CCR-protein of the present invention, or a fragment thereof, in an immunogenic preparation, the immunogen being capable of eliciting an immune response specific for the CCR-protein; e.g. a humoral response, eg. an antibody respone; e.g. a cellular response.

Another aspect of the present invention features recombinant CCR-protein, or a fragment thereof, having an amino acid sequence preferably: at least 60% homologous to the amino acid sequence represented in one of SEQ ID No. 2, 4 or 6; at least 80% homologous to the amino acid sequence represented in one of SEQ ID No. 2, 4 or 6; at least 90% homologous to the amino acid sequence represented in one of SEQ ID No. 2, 4 or 6; identical to the amino acid sequence represented in one of SEQ ID No. 2, 4 or 6. In a preferred embodiment: the fragment comprises at least 5 contiguous amino acid residues of SEQ ID No. 2, 4 or 6; the fragment comprises at least 20 contiguous amino acid residues of SEQ ID No. 2, 4 or 6; the fragment comprises at least 50 contiguous amino acid residues of SEQ ID No. 2, 4 or 6. In a preferred embodiment, the recombinant CCR-protein functions in one of either role of an agonist of cell-cycle regulation or an antagonist of cell-cycle regulation. In a more preferred embodiment: the CCR-protein specifically binds a cyclin dependent kinase (CDK), e.g. specifically binds CDK4; e.g. specifically binds CDK6; e.g. inhibits a kinase acitivity of CDK4; inhibits a kinase acitivity of CDK6; e.g. inhibits phosphorylation of an RB protein by CDK4. In a more preferred embodiment: the CCR-protein regulates a eukaryotic cell-cycle, e.g. a mammalian cell-cycle, e.g., a human cell-cycle; the CCR-protein inhibits proliferation/cell growth of a eukaryotic cell, e.g., a human cell; the CCR-protein inhibits progression of a eukaryotic cell from G1 phase into S phase, e.g., inhibits progression of a mammalian cell from G1 phase into S phase, e.g., inhibits progression of a human cell from G1 phase into S phase; the CCR-protein inhibits the kinase activity of a cyclin dependent kinase (CDK), e.g. a CDK active in G1 phase, e.g. CDK 4; the CCR-protein suppresses tumor growth, e.g. in a tumor cell, e.g. in a tumor cell having an unimpaired RB or RB-like protein checkpoint.

In yet other preferred emboiments, the recombinant CCR-protein is a fusion protein further comprising a second polypeptide portion having an amino acid sequence from a protein unrelated the protein of SEQ ID No. 2, 4 or 6. Such fusion proteins can be functional in a two-hybrid assay.

Another aspect of the present invention provides a substantially pure nucleic acid having a nucleotide sequence which encodes a CCR-protein, or a fragment thereof, having an amino acid sequence at least 60% homologous to one of SEQ ID Nos. 2, 4 or 6. In a more preferred embodiment: the nucleic acid encodes a protein having an amino acid sequence at least 80% homologous to SEQ ID No. 2, more preferably at least 90% homologous to SEQ ID No. 2, and most preferably at least 95% homologous to SEQ ID No. 2; the nucleic acid encodes a protein having an amino acid sequence at least 80% homologous to SEQ ID No. 6, more preferably at least 90% homologous to SEQ ID No. 6, and most preferably at least 95% homologous to SEQ ID No. 6. The nucleic preferably encodes a CCR-protein which specifically binds a cyclin dependent kinase (CDK); e.g. specifically binds CDK4; e.g. specifically binds CDK6; e.g. which inhibits a kinase acitivity of CDK4; e.g. which inhibits phosphorylation of an RB protein by CDK4.

In another embodiment, the nucleic acid hybridizes under stringent conditions to a nucleic acid probe corresponding to at least 12 consecutive nucleotides of SEQ ID No. 1; more preferably to at least 20 consecutive nucleotides of SEQ ID No. 1; more preferably to at least 40 consecutive nucleotides of SEQ ID No. 1.

In a further embodiment, the nucleic acid hybridizes under stringent conditions to a nucleic acid probe corresponding to at least 12 consecutive nucleotides of SEQ ID No. 3; more preferably to at least 20 consecutive nucleotides of SEQ ID No. 3; more preferably to at least 40 consecutive nucleotides of SEQ ID No. 3.

In yet a further embodiment, the nucleic acid hybridizes under stringent conditions to a nucleic acid probe corresponding to at least 12 consecutive nucleotides of SEQ ID No. 5; more preferably to at least 20 consecutive nucleotides of SEQ ID No. 5; more preferably to at least 40 consecutive nucleotides of SEQ ID No. 5.

Furthermore, in certain embodiments, the CCR nucleic acid will comprise a transcriptional regulatory sequence, e.g. at least one of a transcriptional promoter or transcriptional enhancer sequence, operably linked to the CCR-gene sequence so as to render the recombinant CCR-gene sequence suitable for use as an expression vector.

The present invention also features transgenic non-human animals, e.g. mice, which either express a heterologous CCR-gene, e.g. derived from humans, or which mis-express their own CCR-gene, e.g. p16, p15 or p13.5 expression is disrupted. Such a transgenic animal can serve as an animal model for studying cellular disorders comprising mutated or mis-expressed CCR allelles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of one of SEQ ID No. 1, 3 or 5, or naturally occuring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a p16, p15 or p13.5 encoding nucleic acid in a sample of cells isolated from a patient; e.g. for measuring the mRNA level in a cell or determining whether the genomic CCR gene has been mutated or deleted.

The present invention also provides a method for treating an animal having unwanted cell growth characterized by a loss of wild-type CCR-protein function, comprising administering a therapeutically effective amount of an agent able to inhibit a kinase activity of a CDK, e.g. CDK4. In one embodiment, the method comprises administering a nucleic acid construct encoding a CCR protein, e.g. p16, p15 or p13.5, e.g. a polypeptide represented in one of SEQ ID Nos. 2, 4 or 6, under conditions wherein the construct is incorporated by CCR-deficient cells and the polypeptide is expressed, e.g. by gene therapy techniques. In another embodiment, the method comprises administering a CCR mimetic, e.g. a peptidomimetic, which binds to and inhibits the CDK.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a protein represented by one of SEQ ID Nos. 2, 4 or 6, or a homolog thereof; or (ii) the mis-expression of the CCR-gene, e.g. the p16, p15 or p13.5 gene. In preferred embodiments: detecting the genetic lesion comprises ascertaining ,he existence of at least one of a deletion of one or more nucleotides from said gene, an addition of one or more nucleotides to said gene, an substitution of one or more nucleotides of said gene, a gross chromosomal rearrangement of said gene, a gross alteration in the level of a messanger RNA transcript of said gene, the presence of a non-wild type splicing pattern of a messanger RNA transcript of said gene, or a non-wild type level of said protein. For example, detecting the genetic lesion can comprise (i) providing a probe/primer comprising an oligonucleotide containing a region of nucleotide sequence which hybridizes to a sense or antisense sequence of one of SEQ ID Nos. 1, 3 or 5, or naturally occuring mutants thereof, or 5' or 3' flanking sequences naturally associated with the CCR-gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the CCR-gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of said protein is detected in an immunoassay.

Yet another aspect of the invention pertains to a peptidomimetic which binds to a CCR-protein, e.g. p15 or p16, and inhibits its binding to a CDK, e.g. CDK4 or CDK6. For example, a preferred peptidomimetic is an analog of a peptide having the sequence VAEIG(V/E)GAYG(T/K)-V(F/Y)KARD, though more preferably the peptidomimetic is an analog of the hexa-peptide V(F/Y)KARD, and even more preferably of the tetrapeptide KARD. Non-hydrolyzable peptide analogs of such residues can be generated using, for example, benzodiazepine, azepine, substituted gama lactam rings, keto-methylene pseudopeptides, β-turn dipeptide cores, or β-aminoalcohols.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press:1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

BRIEF DESCRIPTION OF THE DRAWINGS

FIGS. 1A–1B are a schematic representation of the p16 cDNA, indicating the location of exon boundaries and PCR primers used in the present invention.

FIGS. 2A and 2B are the genomic nucleic acid sequence for exon 1 and the non-coding sequences directly flanking exon 1. The sequence is a composite sequence from several primers. FIG. 2C is the genomic sequence about exon 2.

FIGS. 3A–3C are the genomic nucleic acid sequence for exon 3 and the non-coding sequences directly flanking exon 3. The sequence is a composite sequence from several primers.

FIG. 4 illustrates the loss of p16 sequences from the genomes of several human tumor cells, as compared to normal human controls and other human tumors.

FIG. 6 is a sequence alignment of a highly conserved portion of the CCR-proteins p16, p15 and p13.5.

DETAILED DESCRIPTION OF THE INVENTION

Figure 5:
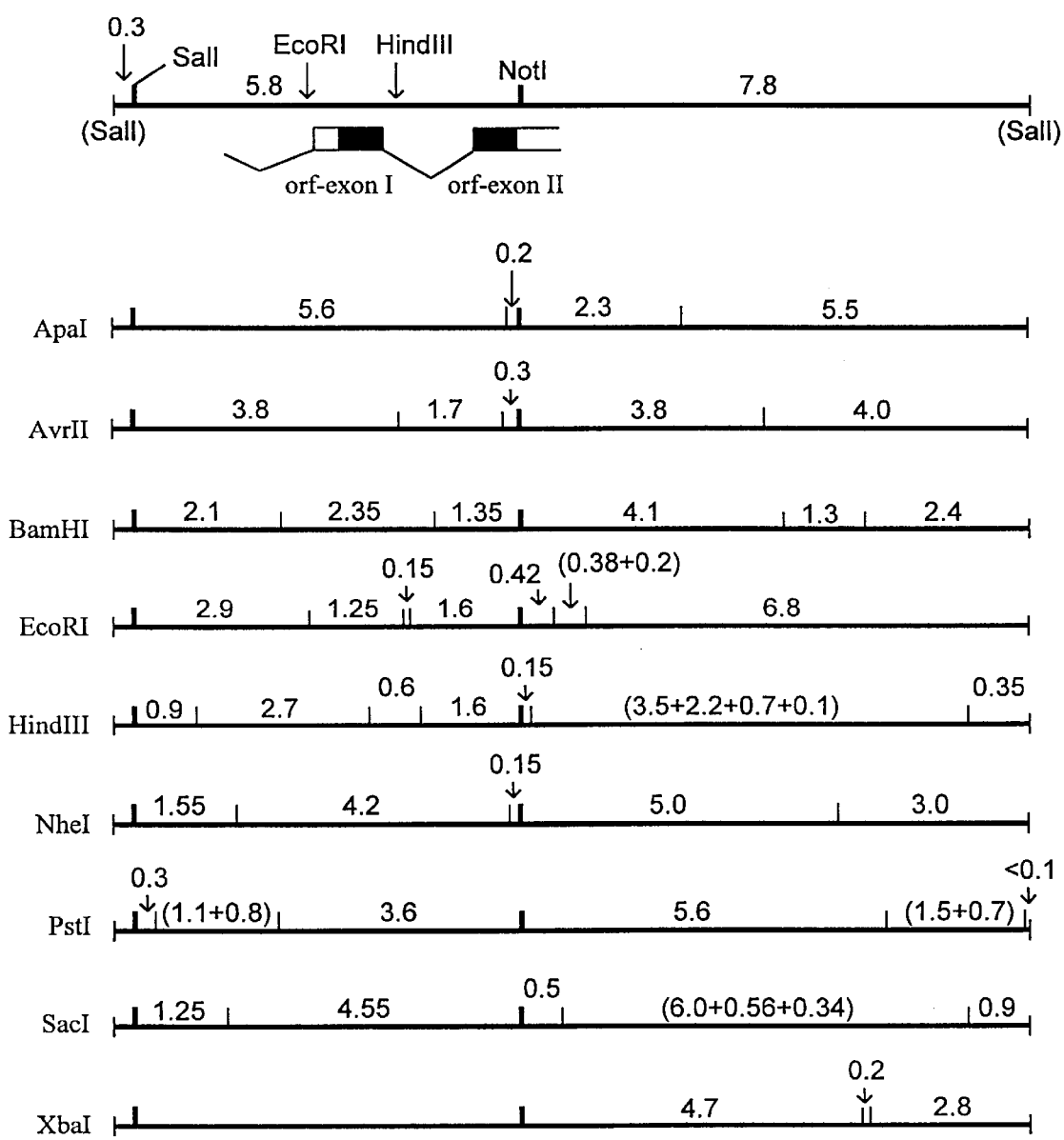
FIG. 5 illustrates the restriction map for the mouse p16 gene.

Progression through the cell-cycle is marked by a series of irreversible transitions that separate discrete tasks necessary for faithful cell duplication. These transitions are negatively regulated by signals that constrain the cell-cycle until specific conditions are fulfilled. Entry in to mitosis, for example, is inhibited by incompletely replicated DNA or DNA damage. These restriction on cell-cycle progression are essential for preserving the fidelity of the genetic information during cell division. The transition from $G_1$ to S phase, on the other hand, coordinates cell proliferation with environmental cues, after which the checks on the cell-cycle progression tend to be cell autonomous. Among the signals that restrict cell-cycle progression during $G_1$ are extracellular proteins which inhibit cell proliferation, growth factor or amino acid depletion, and cell-cell contact. Disruption of these signalling pathways uncouples cellular responses from environmental controls and may lead to unrestrained cell proliferation.

Eukaryotic cells, in general, require cyclin-dependent kinases (CDKs) for progression through $G_1$ and entry into S phase. In mammalian cells, both D- and E-type cyclins are rate limiting for the $G_1$ to S transition, and both reduce, but do not eliminate, the cell's requirement for mitogenic growth factors. However, prior to the present discovery, there was little information concerning the manner by which these cyclins and CDKs are negatively regulated by either intracellular or extracellular signals that inhibit cell proliferation.

The present invention is directed to the discovery of a family of related cell-cycle regulatory proteins (termed "CCR-proteins") which function typically to restrict progression of a cell through mitosis, and are likely to be involved in controlling progression through meiosis. Members of this family, apparently evolutionarily related, include a polypeptide (termed "p16") having an apparent molecular weight of 16 Kd, another polypeptide (termed "p15") having an approximate molecular weight of 15 Kd, and a 13.5 Kd polypeptide (termed "p13.5"). The nucleotide sequences for the human p16, the human p15, and the mouse p13.5 coding sequences are provided in SEQ ID Nos. 1, 3 and 5, respectively, and a apartial sequence for a mouse p16/p15 clone is provided in SEQ ID No. 7. The corresponding amino acid sequences are represented in SEQ ID Nos. 2, 4, 6 and 8. Moreover, data from hybridization and immunoprecipitation experiments indicates still other members of the CCR-protein family exist.

One function of members of this family of proteins in cell-cycle regulation is in modulating the activity of cyclin/CDK complexes during various stages of the cell-cycle, particularly those which include CDKs active in $G_1$ phase, such as CDK4 or CDK6. To illustrate, both p16 and p15 are demonstrated below to exert an inhibitory effect on the activity of cyclin/CDK complexes, particularly those which include CDK4 or CDK6. For instance, each protein is able to inhibit the activity of cyclin D1/CDK complexes in vivo. As is generally known, cyclin D1 has been associated with a wide variety of proliferative diseases. Consequently, the present invention identifies a potential inhibitor of cell proliferation resulting from oncogenic expression of cyclin D1. Moreover, the diversity of members of the CCR-protein family, like the diversity of CDKs, is suggestive of individualistic roles of each member of this family, which may be tissue-type of cell-type specific, occur at different points in the cell-cycle, occur as part of different extracellular or intracellular signalling pathways, or a combination thereof.

As described in the examples below, certain of the CCR-proteins have been shown to be deleted or mutated at high frequency in tumors, such as derived from lung, breast, brain, bone, skin, bladder, kidney, ovary, or lymphocytes. Consequently, as set forth in the present application, replacement of CCR protein function by gene therapy or by CCR mimeties, or by direct inhibition of CDK4 or CDK6 activity, is therefore a potential therapy for treating such proliferative disorders. Moreover, the present data demonstrates that p15 expression is regulated by treatment with transforming growth factor-beta (TGF-β), suggesting that p15 may function as an effector of TGF-β mediated cell cycle arrest via inhibition of CDK4 or CDK6 kinases. Considered in light of recent findings demonstrating that reduced responsiveness to TGF-β may be an important event in the loss of growth control in many proliferative disorders, an approach to modulate CDK4/6 activity by CCR mimetics or CCR-gene therapy, or by mechanism based inhibitors of the kinases themselves, is even more attractive for treating such proliferative disorders.

Accordingly, the present invention makes available diagnostic and therapeutic assays and reagents for detecting and treating proliferative disorders arising from, for example, tumorigenic transformation of cells, or other hyperplastic or neoplastic transformation processes, as well as differentiative disorders, such as degeneration of tissue, e.g. neurodegeneration. For example, the present invention makes available reagents, such as antibodies and nucleic acid probes, for detecting altered complex formation, and/or altered levels of CCR-protein expression, and/or CCR-gene deletion or mutation, in order to identify transformed cells. Moreover, the present invention provides a method of treating a wide variety of pathological cell proliferative conditions, such as by gene therapy utilizing recombinant gene constructs encoding the subject CCR-proteins, or by providing CCR-mimetics, with the general strategy being the inhibition of abherently proliferating cells.

The subject proteins can also be used in assay systems to identify agents which either decrease the ability of the CCR-protein to bind a CDK (e.g. CDK4 or CDK6) and thereby relieve inhibition of cyclin/CDK complexes, or alternatively, which agonize or mimic the CCR-mediated inhibition of CDK activation. In the latter, e.g. CCR mimetics, the consequence of inhibiting activation of a cyclin/CDK complex, e.g. cyclin D/CDK4, is the failure of the cell to advance through the cell-cycle, which inhibition can lead ultimately to cell death. Reactivation of the CDK/cyclin complexes, on the otherhand, can disrupt or otherwise unbalance the cellular events occuring in a transformed cell. Such agents can be of use therapeutically to activate CDK4 complexes in cells transformed, for example, by tumor viruses. Treatment of such cells can cause premature progression through a checkpoint, e.g. the retinoblastoma (RB) checkpoint, and result in mitotic catastrophe (cell death) or induction of apoptosis.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an open reading frame encoding a cell-cycle regulatory of the present invention, including both exon and (optionally) intron sequences. In preferred embodiments, the nucleic acid is DNA or RNA. Exemplary recombinant genes include nucleic acids which encode all or a CDK-binding portion of the p16 protein represented in SEQ ID No. 2, the p15 protein represented in SEQ ID No. 4, or the p13.5 protein represented in SEQ ID No. 6. The term "intron" refers to a DNA sequence present in a given CCR-gene which is not translated into protein and is generally found between exons.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of one of the subject cell-cycle regulatory proteins, e.g. p16, p15 or p13.5.

"Cells" or "cell cultures" or "recombinant host cells" or "host cells" are often used interchangeably as will be clear from the context. These terms include the immediate subject cell which expresses the cell-cycle regulatory protein of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant CCR-protein.

As used herein, the term "vector" refers to a nucleic acid molecule capable of transporting another nucleic acid to which it has been linked. The term "expression vector" includes plasmids, cosmids or phages capable of synthesizing the subject CCR-protein encoded by the respective recombinant gene carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In preferred embodiments, transcription of a recombinant CCR-gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a neuronal lineage, e.g. glial cells, or alternatively, in epithelial cells, e.g. melanocytes. In an illustrative embodiment, gene constructs utilizing glial-specific promoters can be used as a part of gene therapy to cause expression of recombinant forms of one of the subject CCR-proteins in glioma cells with a feature of the gene construct being a tissue-specific promoter for directing expression of the subject protein in only glial tissue. The term also covers so-called "leaky" promoters, which regulate expression of a selected DNA primarily in one tissue, but cause expression in other tissues as well.

As used herein, a "transgenic animal" is any animal, preferably a non-human mammal in which one or more of the cells of the animal contain heterologous nucleic acid introduced by way of human intervention, such as by trangenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of the subject CCR proteins, e.g. either agonistic or antagonistic forms, or in which an endogenous CCR-gene has been disrupted. However, transgenic animals in which the recombinant CCR-gene is silent are also contemplated, as for example, the FLP or CRE recombinase dependent constructs described below. The "non-human animals" of the invention include vertebrates such as rodents, non-human primates, sheep, dog, cow, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that the recombinant CCR-gene is present and/or expressed, or disrupted, in some tissues but not others.

As used herein, the term "transgene" means a nucleic acid sequence (encoding, e.g., a CCR-polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As used herein, the terms "transforming growth factor-beta" and "TGF-β" denote a family of structurally related paracrine polypeptides found ubiquitously in vertebrates, and prototypic of a large family of metazoan growth, differentiation, and morphogenesis factors (see, for review, Massaque et al. (1990) *Ann Rev Cell Biol* 6:597–641; and Sporn et al. (1992) *J Cell Biol* 119:1017–1021).

The term "evolutionarily related to", with respect to nucleic acid sequences encoding CCR-proteins, refers to nucleic acid sequences which have arisen naturally in an organism, including naturally occurring mutants. The term also refers to nucleic acid sequences which, while derived from a naturally occurring CCR-proteins, have been altered by mutagenesis, as for example, combinatorial mutagenesis described below, yet still encode polypeptides which have at least one activity of a CCR-protein. For instance, the sequence of p16 can be altered by mutagenesis based on amino acid substitutions derived from alignment with the p15 and/or p13.5 sequences.

One aspect of the present invention pertains to an isolated nucleic acid comprising the nucleotide sequence encoding a CCR-protein, fragments thereof encoding polypeptides having at least one biological activity of a CCR-protein, and/or equivalents of such nucleic acids. The term nucleic acid as used herein is intended to include such fragments and equivalents. The term equivalent is understood to include nucleotide sequences encoding functionally equivalent CCR-proteins or functionally equivalent peptides having an activity of a CCR-protein such as described herein. Equivalent nucleotide sequences will include sequences that differ by one or more nucleotide substitutions, additions or deletions, such as allelic variants; and will also include sequences that differ from the nucleotide sequence encoding the subject p16 protein represented by SEQ ID No. 2, or the p15 protein represented by SEQ ID No. 4, or the p13.5 protein represented by SEQ ID No. 6 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1 M salt) to the nucleotide sequence of a CCR-gene shown in SEQ ID No. 1, 3 or 5. In one embodiment, equivalents will further include nucleic acid sequences derived from and evolutionarily related to the nucleotide sequence shown in one of SEQ ID No. 1, 3 or 5.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding on of the subject CCR-proteins preferably includes no more than 10 kilobases (kb) of nucleic acid sequence which naturally immediately flanks the CCR-gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Polypeptides referred to herein as having an activity of a cell-cycle regulatory protein preferably have an amino acid sequence corresponding to all or a portion of the amino acid sequence of the p16 protein shown in SEQ ID No. 2, of the p15 protein shown in SEQ ID No. 4, or of the p13.5 protein shown in SEQ ID No. 6, or isoforms of one of these proteins (including differential splicing variants). In preferred embodiments, the biological activity of a CCR-protein includes an ability to regulate a eukaryotic cell-cycle, e.g. a mammalian cell-cycle, e.g., a human cell-cycle; an ability to inhibit proliferation/cell growth of a eukaryotic cell, e.g. a mammalian cell, e.g., a human cell; an ability to inhibit progression of a eukaryotic cell from G1 phase into S phase, e.g., inhibit progression of a mammalian cell from G1 phase into S phase, e.g., inhibit progression of a human cell from G1 phase into S phase; an ability to inhibit the kinase activity of a cyclin dependent kinase (CDK), e.g. a CDK active in G1 phase, e.g. CDK4, e.g. CDK6; e.g. an ability to inhibit phosphorylation of a retinoblastoma (RB) or retinoblastoma-like protein by a cyclin dependent kinase. Moreover, CCR-proteins of the present invention may also have biological activities which include: an ability to suppress tumor growth, e.g. in a tumor having an unimpaired RB protein; an ability to regulate cell-cycle progression in response to extracellular factors and cytokines, e.g. functional in paracrine or autocrine regulation of cell growth and/or differentiation, e.g. inhibit CDK activation in response to transforming growth factor-β (TGF-β) or related growth, differentiation or morphogenesis factor. In this respect, the CCR-proteins of the present invention may also function to prevent de-differentiation of cells/tissue. Other biological activities of the subject CCR-proteins are described herein or will be reasonably apparent to those skilled in the art in light of the present disclosure.

Moreover, it will be generally appreciated that, under certain circumstances, it will be advantageous to provide homologs of naturally-occurring forms of particular CCR-proteins which are either agonists or antagonists of only a subset of that protein's biological activities. Thus, specific biological effects can be elicited by treatment with a homolog of limited function, and with fewer side effects relative to treatment with agonists or antagonists which are directed to all of the biological activities of that protein. For example, p16 homologs can be generated which bind to and inhibit activation of CDK4 without substantially interfering with the activation of CDK6.

In one embodiment, the nucleic acid of the invention encodes a peptide which is an agonist or antagonist of the p16 protein and comprises an amino acid sequence shown in SEQ ID No. 2. Preferred nucleic acids encode a peptide having a p16 protein activity and being at least 60% homologous, more preferably 70% homologous and most preferably 80% homologous with an amino acid sequence shown in SEQ ID No. 2. Nucleic acids which encode peptides having an activity of a p16 protein and having at least about 90%, more preferably at least about 95%, and most preferably at least about 98–99% homology with a sequence shown in SEQ ID No. 2 are also within the scope of the invention. Preferably, the nucleic acid is a cDNA molecule comprising at least a portion of the nucleotide sequence encoding a p16 protein shown in SEQ ID No. 1. A preferred portion of the cDNA molecule shown in SEQ ID No. 1 includes the coding region of the molecule.

In another embodiment, the nucleic acid of the invention encodes a peptide which is an agonist or antagonist of the p15 protein and comprises an amino acid sequence shown in SEQ ID No. 4. Preferred nucleic acids encode a peptide having a p15 protein activity and being at least 60% homologous, more preferably 70% homologous and most preferably 80% homologous with an amino acid sequence shown in SEQ ID No. 4. Nucleic acids which encode peptides having an activity of a p15 protein and having at least about 90%, more preferably at least about 95%, and most preferably at least about 98–99% homology with a sequence shown in SEQ ID No. 4 are also within the scope of the invention. In a representative embodiment, the nucleic acid is a cDNA molecule comprising at least a portion of the nucleotide sequence encoding a p15 protein shown in SEQ ID No. 3. A preferred portion of the cDNA molecule shown in SEQ ID No. 3 includes the coding region of the molecule.

In yet another embodiment, the nucleic acid of the invention encodes a peptide having an activity of a p13.5 protein and comprising an amino acid sequence shown in SEQ ID No. 6. Preferred nucleic acids encode a peptide having a p13.5 protein activity and being at least 60% homologous, more preferably 70% homologous and most preferably 80% homologous with an amino acid sequence shown in SEQ ID No. 6. Nucleic acids which encode peptides having an activity of a p13.5 protein, such as the ability to bind a CDK, and having at least about 90%, more preferably at least about 95%, and most preferably at least about 98–99% homology with a sequence shown in SEQ ID No. 6 are also within the scope of the invention. Preferably, the nucleic acid is a cDNA molecule comprising at least a portion of the nucleotide sequence encoding a p13.5 protein shown in SEQ ID No. 5. A preferred portion of the cDNA molecule shown in SEQ ID No. 5 includes the coding region of the molecule.

In yet another embodiment, the nucleic acid of the invention encodes a peptide having an amino acid sequence shown in SEQ ID No. 8. Preferred nucleic acids encode a peptide having a CCR-protein activity and being at least 60% homologous, more preferably 70% homologous and most preferably 80% homologous with an amino acid sequence shown in SEQ ID No. 8. Nucleic acids which encode peptides having an activity of a CCR-protein, such as the ability to bind a CDK, and having at least about 90%, more preferably at least about 95%, and most preferably at least about 98–99% homology with a sequence shown in SEQ ID No. 8 are also within the scope of the invention. Preferably, the nucleic acid is a cDNA molecule comprising the nucleotide sequence shown in SEQ ID No. 7.

Another aspect of the invention provides a nucleic acid which hybridizes under high or low stringency conditions to a nucleic acid which encodes a CCR polypeptide having all or a portion of an amino acid sequence shown in one of SEQ ID Nos. 2, 4, 6 or 8. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids which differ from the nucleotide sequencse shown in one of SEQ ID Nos. 1, 3, 5 or 7 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject CCR-proteins will exist among eukaryotic cells. One skilled in the art will appreciate that these variations in one or more nucleotides (up to about 3–4% of the nucleotides) of the nucleic acids encoding a particular member of the CCR-protein family may exist among individuals of a given species due to natural allelic variation. Any and all such nucleotide variations and resulting amino acid polymorphisms are within the scope of this invention.

Fragments of the nucleic acid encoding a biologically active portion of the subject CCR-proteins are also within the scope of the invention. As used herein, a fragment of the nucleic acid encoding an active portion of a CCR-protein refers to a nucleotide sequence having fewer nucleotides than the nucleotide sequence encoding the full length amino acid sequence of, for example, the CCR-proteins represented in SEQ ID Nos. 2, 4 or 6, and which encodes a peptide which retains at least a portion of the bioligical activity of the full-length protein (i.e., a peptide capable of binding a CDK) as defined herein, or alternatively, which is functional as an antagonist of the bioligical activity of the full-length protein. Nucleic acid fragments within the scope of the invention include those capable of hybridizing under high or low stringency conditions with nucleic acids from other species, e.g. for use in screening protocols to detect homologs of the subject CCR-proteins. Nucleic acids within the scope of the invention may also contain linker sequences, modified restriction endonuclease sites and other sequences useful for molecular cloning, expression or purification of such recombinant peptides.

As indicated by the examples set out below, a nucleic acid encoding a peptide having an activity of a CCR-protein may be obtained from mRNA or genomic DNA present in any of a number of eukaryotic cells in accordance with protocols described herein, as well as those generally known to those skilled in the art. A cDNA encoding a CCR-protein, for example, can be obtained by isolating total mRNA from a cell, e.g. a mammalian cell, e.g. a human cell. Double stranded cDNAs can then be prepared from the total mRNA, and subsequently inserted into a suitable plasmid or bacteriophage vector using any one of a number of known techniques. A gene encoding a CCR-protein can also be cloned using established polymerase chain reaction techniques in accordance with the nucleotide sequence information provided by the invention. A preferred nucleic acid is a cDNA encoding a p16 protein having a sequence shown in SEQ ID No. 1. Another preferred nucleic acid is a cDNA encoding a p15 protein having a sequence shown in SEQ ID No. 3. Yet another preferred nucleic acid is a cDNA encoding a p13.5 protein having a sequence shown in SEQ ID No. 5.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding a CCR-protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a CCR-protein. Alternatively, the antisense construct is an oligonucleotide probe which is generated ex vivo and which, when introduced into the cell causes inhibition of expression by hybridizing with the mRNA and/or genomic sequences encoding one of the subject CCR proteins. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneuos for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

This invention also provides expression vectors comprising a nucleotide sequence encoding a subject cell-cycle regulatory protein and operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of a CCR-protein. Accordingly, the term regulatory sequence includes promoters, enhancers and other expression control elements. Exemplary regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the CCR-proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda , the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

As will be apparent, the subject gene constructs can be used to cause expression of the subject CCR-proteins in cells propagated in culture, e.g. to produce proteins or peptides, including fusion proteins or peptides, for purification. In addition, recombinant expression of the subject CCR-proteins, or agonist forms thereof, in cultured cells can be useful for preventing de-differentiation of cells in vitro. To illustrate, in vitro neuronal culture systems have proved to be fundamental and indispensable tools for the study of neural development, as well as the identification of neurotrophic factors. Once a neuronal cell has become terminally-differentiated, it typically will not change to another terminally differentiated cell-type. However, neuronal cells can nevertheless readily lose their differentiated state. This is commonly observed when they are grown in culture from adult tissue, and when they form a blastema during regeneration.

Agonizing the function of the subject CCR-proteins, such as by maintaining expression (or overexpression) of p16 or p15, provides a means for ensuring an adequately restrictive environment in order to maintain neuronal cells at various stages of differentiation, and can be employed, for instance, in cell cultures designed to test the specific activities of trophic factors. Other tissue culture systems which require maintenance of differentiation will be readily apparent to those skilled in the art In this respect, each of the agonist and antagonist of CCR inhibition of CDK4 and CDK6 can be used for ex vivo tissue generation, as for example, to enhance the generation of prosthetic cartilage devices for implantation.

Conversely, by antagonizing the activity of the wild-type CCR-proteins, such as by expression of antagonistic homologs, antisense constructs, or treatment with agents able to disrupt binding of a CCR-protein with a CDK, the cultured cells can be prevented from following certain differentiative pathways, and, importantly, can cause transformation of cells in culture. In similar fashion, the dominant negative CDK4 and CDK6 mutants described below can be used to cause cellular transformation, as each of these CDK mutants is insensitive to p16 inhibition and is effectively an antagonist of p16. The ability of CCR antagonists to promote cell growth is particularly significant in light of the observation that human cells are notoriously difficult to grow in vitro. Accordingly, such reagents are therefore useful for transforming, and in certain instances, immortalizing, cells from primiary cell cultures.

Moreover, the subject gene constructs can also be utilized in diagnostic assays to determine if a cell's growth is no longer dependent on the regulatory function of a CCR-protein, e.g. in determining the phenotype of a transformed cell. To illustrate, a sample of cells from the tissue can be obtained from a patient and dispersed in appropriate cell culture media, a portion of the cells in the sample can be caused to express a recombinant CCR-protein, e.g. by transfection with a p16, p15 or p13.5 expression vector, and subsequent growth of the cells assessed. The ability of cells to proliferate despite expression of the CCR-protein is indicative of a lack of dependance on cell regulatory pathways which include the CCR-protein, e.g. RB-mediated checkpoints Depending on the nature of the tissue of interest, the sample can be in the form of cells isolated from, for example, a blood sample, an exfoliated cell sample, a fine needle aspirant sample, or a biopsied tissue sample. Where the initial sample is a solid mass, the tissue sample can be minced or otherwise dispersed so that cells can be cultured, as is known in the art. Such knowledge can have both prognostic and therapeutic benefits.

This invention also pertains to a host cell transfected with a recombinant CCR-gene in order to express a polypeptide having an activity of a CCR-protein. The host cell may be any prokaryotic or eukaryotic cell. For example, a CCR-protein of the present invention may be expressed in bacterial cells such as E. coli, insect cells (baculovirus), yeast, or mammalian cells. Other suitable host cells are known to those skilled in the art.

Another aspect of the present invention concerns recombinant CCR-proteins which are encoded by genes derived from eukaryotic organisms, e.g. mammals, e.g. humans, and which have at least one biological activity of a CCR-protein, or which are naturally occurring mutants thereof. The term "recombinant protein" refers to a protein of the present invention which is produced by recombinant DNA techniques, wherein generally DNA encoding the CCR-protein is inserted into a suitable expression vector which is in turn used to transform a host cell to produce the heterologous protein. Moreover, the phrase "derived from", with respect to a recombinant gene encoding the recombinant CCR-protein, is meant to include within the meaning of "recombinant protein" those proteins having an amino acid sequence of a native CCR-protein, or an amino acid sequence similar thereto which is generated by mutations including substitutions and deletions of a naturally occurring CCR-protein of a organism. To illustrate, recombinant proteins preferred by the present invention, in addition to native p16, p15 or p13.5 proteins, are those recombinantly produced proteins which are at least 60% homologous, more preferably 70% homologous and most preferably 80% homologous with an amino acid sequence shown in SEQ ID No. 2, 4, 6 or 8. Polypeptides having an activity of a CCR-protein, such as CDK-binding, and having at least about 90%, more preferably at least about 95%, and most preferably at least about 98–99% homology with a sequence shown in SEQ ID No. 2, 4, 6 or 8 are also within the scope of the invention. Thus, the present invention pertains to recombinant CCR-proteins which are encoded by genes derived from a organism and which have amino acid sequences evolutionarily related to a CCR-protein represented by one of ID No. 2, 4 or 6, wherein "evolutionarily related to", refers to CCR-proteins having amino acid sequences which have arisen naturally (e.g. by allelic variance or by differential splicing), as well as mutational variants of CCR-proteins which are derived, for example, by combinatorial mutagenesis.

The present invention further pertains to methods of producing the subject CCR-proteins. For example, a host cell transfected with expression vector encoding one of the subject CCR-protein can be cultured under appropriate conditions to allow expression of the peptide to occur. The peptide may be secreted and isolated from a mixture of cells and medium containing the peptide. Alternatively, the peptide may be retained cytoplasmically and the cells harvested, lysed and the protein isolated. A cell culture includes host cells, media and other byproducts. Suitable media for cell culture are well known in the art. The peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for particular epitopes of the subject CCR-proteins. In a preferred embodiment, the CCR-protein is a fusion protein containing a domain which facilitates its purification, such as p16-GST, p15-GST, or a p13.5-GST fusion proteins.

Thus, a nucleotide sequence derived from the cloning of a CCR-protein of the present invention, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant CCR-proteins, or portions thereof, by microbial means or tissue-culture technology in accord with the subject invention.

The recombinant CCR-protein can be produced by ligating the cloned gene, or a portion thereof, into a vector suitable for expression in either prokaryotic cells, eukaryotic cells, or both. Expression vehicles for production of a recombinant CCR-protein include plasmids and other vectors. For instance, suitable vectors for the expression of p16, p15 or p13.5 include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press:1989) Chapters 16 and 17. In some instances, it may be desirable to express the recombinant CCR-protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a carboxy terminal fragment of the full-length CCR-protein is desired, i.e. a trunction mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718-1722). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of one of the subject CCR-proteins. For example, the VP6 capsid protein of rotavirus can be used as an immunologic carrier protein for portions of polypeptide, either in the monomeric form or in the form of a viral particle. The nucleic acid sequences corresponding to the portion of the CCR protein to which antibodies are to be raised can be incorporated into a fusion gene construct which includes coding sequences for a late vaccinia virus structural protein to produce a set of recombinant viruses expressing fusion proteins comprising a portion of the protein as part of the virion. The Hepatitis B surface antigen can also be utilized in this role as well. Similarly, chimeric constructs coding for fusion proteins containing a portion of a CCR-protein and the poliovirus capsid protein can be created to enhance immunogenicity (see, for example, EP Publication No. 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can be utilized, wherein a desired portion of a CCR-protein is obtained directly from organo-chemical synthesis of the peptide onto an oligomeric branching lysine core (see, for example, Posnett et al. (1988) *J B C* 263:1719 and Nardelli et al. (1992) *J. Immunol.* 148:914). Antigenic determinants of the CCR-proteins can also be expressed and presented by bacterial cells.

In addition to utilizing fusion proteins to enhance immunogenicity, it is widely appreciated that fusion proteins can also facilitate the expression of proteins. For example, the CCR-protein of the present invention can be generated as a glutathione-S-transferase (GST) fusion proteins. Such GST fusion proteins can be used to simply purification of the CCR-protein, such as through the use of glutathione-derivatized matrices (see, for example, *Current Protocols in Molecular Biology*, eds. Ausabel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified CCR-protein (e.g., see Hochuli et al. (1987) *J. Chromatography* 411:177; and Janknecht et al. *PNAS* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

The present invention also makes available isolated and/or purified forms of the subject CCR-proteins, which are isolated from, or otherwise substantially free of other extracellular proteins, especially cell-cycle proteins, e.g. CDKs, cyclins, p21, p19, or PCNA, normally associated with the CCR-protein. The term "substantially free of other cellular proteins" (also referred to herein as "contaminating proteins") is defined as encompassing, for example, p16, p15 or p13.5 preparations comprising less than 20% (by dry weight) contaminating protein, and preferably comprises less than 5% contaminating protein. Functional forms of the CCR-proteins can be prepared, for the first time, as purified preparations by using a cloned gene as described herein. By "purified", it is meant, when referring to a polypeptide, that the indicated molecule is present in the substantial absence of other biological macromolecules, such as other proteins (particularly other cycle proteins such as CDK4 or CDK6, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

Moreover, isolated peptidyl portions of the subject CCR-proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a CCR-protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of, for example, CDK4 activation, such as by microinjection assays. In an illustrative embodiment, peptidyl portions of the subject CCR proteins can tested for CDK-binding activity, as well as inhibitory ability, by expression as, for example, thioredoxin fusion proteins each of which contains a discrete fragment of the CCR-protein (see, for example, U.S. Pat. Nos. 5,270,181 and 5,292,646; and PCT publication WO94/02502).

It is also possible to modify the structure of the subject CCR-proteins for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the cell-cycle regulatory proteins described in more detail herein. Such modified polypeptides can be produced, for instance, by amino acid substitution, deletion, or addition.

Moreover, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide= asparagine, glutamine; and (6) sulfur-containing=cysteine and methionine. (see, for example, *Biochemistry*, 2nd ed, Ed. by L. Stryer, W H Freeman and Co.:1981). Whether a change in the amino acid sequence of a peptide results in a functional homolog can be readily determined by assessing the ability of the variant peptide to produce a response in cells in a fashion similar to the wild-type protein. For instance, such variant forms of p16 can be assessed for their ability to complement a p16-deficient cell. Peptides in which more than one replacement has taken place can readily be tested in the same manner.

This invention further contemplates a method of generating sets of combinatorial mutants of the present CCR-proteins, as well as truncation mutants, and is especially useful for identifying potential variant sequences (e.g. homologs) that are functional in binding to a CDK, especially CDK4 or CDK6. The purpose of screening such combinatorial libraries is to generate, for example, novel p16, p15 or p13.5 homologs which can act as either agonists or antagonist, or alternatively, possess novel activities all together. To illustrate, p16 and/or p15 homologs can be engineered by the present method to provide more efficient binding to CDK4, yet have a significantly reduced binding affinity for CDK6 relative to the naturally-occurring form of the protein. Thus, combinatorially-derived homologs can be generated which have a selective potency relative to a naturally occurring CCR-protein. Such proteins, when expressed from recombinant DNA constructs, can be used in gene therapy protocols.

Likewise, mutagenesis can give rise to CCR homologs which have intracellular half-lives dramatically different than the corresponding wild-type protein. For example, the altered protein can be rendered either more stable or less stable to proteolytic degradation or other cellular process which result in destruction of, or otherwise inactivation of, the CCR-protein. Such homologs, and the genes which encode them, can be utilized to alter the envelope of p16, p15 or p13.5 expression by modulating the half-life of the protein. For instance, a short half-life can give rise to more transient biological effects and, when part of an inducible expression system, can allow tighter control of recombinant CCR-protein levels within the cell. As above, such proteins, and particularly their recombinant nucleic acid constructs, can be used in gene therapy protocols.

In similar fashion, CCR homologs can be generated by the present combinatorial approach to act as antagonists, in that they are able to interfere with the ability of the corresponding wild-type protein to regulate cell proliferation.

In a representative embodiment of this method, the amino acid sequences for a population of CCR-protein homologs are aligned, preferably to promote the highest homology possible. Such a population of variants can include, for example, p16 and/or p15 homologs from one or more species, or homologs from the same species but which differ due to mutation. Amino acids which appear at each position of the aligned sequences are selected to create a degenerate set of combinatorial sequences. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned.

To illustrate, upon inspection of the p16, p15 and p13.5 sequences (see FIG. 6), it was noted that an internal fragment of the three CCR-proteins was highly conserved. Based on these alignments, combinatorial libaries can be generated from this portion, the members of which can be expressed in the absence of other portions of a CCR-protein, or as a part of a CCR-protein in which other portions of the protein are static (e.g. a p16 or p15 protein in which only residues Met-52 to Gly-135 or Met-53 to Gly-136, respectively, are varied by combinatorial mutagenesis). For instance, a library of p16 or p15 proteins comprise an amino acid sequence represented by the degenerate amino acid sequence:

Met-Met-Met-Gly-Xaa(1)-Xaa(2)-Xaa(3)-Val-Ala-Xaa(4)-Leu-Leu-Leu-

Xaa(5)-Xaa-(6)-Gly-Ala-Xaa(7)-Xaa(8)-Asn-Cys-Xaa(9)-Asp-Pro-Xaa(10)-

Thr-Xaa(11)-Xaa(12)-Xaa(13)-Arg-Pro-Val-His-Asp-Ala-Ala-Arg-Glu-Gly-

Phe-Leu-Asp-Thr-Leu-Val-Val-Leu-His-Xaa(14)-Xaa(15)-Gly-Ala-Arg-Leu-

Asp-Val-Arg-Asp-Ala-Trp-Gly-Arg-Leu-Pro-Xaa(16)-Asp-Leu-Ala-Xaa(17)-

Glu-Xaa(18)-Gly-His-Xaa(19)-Asp-Xaa-(20)-Xaa(21)-Xaa(22)-Tyr-Leu-Arg-

Xaa(23)-Ala-Xaa(24)-Gly wherein each of Xaa(1)-Xaa(24) is selected from one of the amino acid residues of the same position in SEQ ID No. 2, 4 or 6.

Further expansion of the combinatorial library can be made by, for example, by including amino acids which would represent conservative mutations at one or more of the degenerate positions. Inclusion of such conservative mutations can give rise to a library of potential cell-cycle regulatory sequences represented by the above formaula, but wherein Xaa(1) represents Ser, Thr, Asn or Gln; Xaa(2) represents Gly, Ala, Val, Leu, or Ile; Xaa(3) represents Arg, Lys or His; Xaa(4) represents Gly, Ala, Val, Leu, lie, Asp or Glu; Xaa(5) represents Gly, Ala, Val, Leu, Ile, Asn or Gln; Xaa(6) represents Arg, Lys, His, Tyr or Phe; Xaa(7) represents Asp or Glu; Xaa(8) represents Pro, Gly, Ser or Thr; Xaa(9) represents Gly, Ala, Val, Leu, Ile, Asp or Glu; Xaa(10) represents Gly, Ala, Val, Leu, Ile, or an amino acid gap; Xaa(11) represents Gly, Ala, Val, Leu, Ile, Ser or Thr; Xaa(12) represents Phe, Tyr, Trp or an amino acid gap; Xaa(13) represents Ser or Thr; Xaa(14) represents Gly, Ala, Val, Leu, Ile, Arg, Lys or His; Xaa(15) represents Gly, Ala, Val, Leu, Ile, Ser or Thr; Xaa(16) represents Gly, Ala, Val, Leu or Ile; Xaa(17) represents Glx; Xaa(18) represents Gly, Ala, Val, Leu, Ile, Lys, His or Arg; Xaa(19) represents Arg or Gln; Xaa(20) represents Gly, Ala, Val, Leu or Ile; Xaa(21) represents Gly, Ala, Val, Leu or Ile; Xaa(22) represents Gly, Ala, Val, Leu, Ile, Lys, His or Arg; Xaa(23) represents Gly, Ala, Val, Leu, Ile, Thr or Ser; Xaa(24) represents Gly, Ala, Val, Leu, Ile, Ser, Thr or an amino acid gap, where in this context, an amino acid gap is understood to mean the deletion of that amino acid position from the polypeptide. Alternatively, amino acid replacement at degenerate positions can be based on steric criteria, e.g. isosteric replacement, without regard for polarity or charge of amino acid sidechains. Similarly, completely random mutagenesis of one or more of the variant positions (Xaa) can be carried out.

In a preferred embodiment, the combinatorial CCR library is produced by way of a degenerate library of genes encoding a library of polypeptides which each include at least a portion of potential CCR-protein sequences. For instance, a mixture of synthetic oligonucleotides can be enzymatically ligated into gene sequences such that the degenerate set of potential CCR nucleotide sequences are expressible as individual polypeptides, or alternatively, as a set of larger fusion proteins (e.g. for phage display) containing the set of CCR protein sequences therein.

There are many ways by which the library of potential CCR homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential CCR sequences. The synthesis of degenerate oligonucleotides is well known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87:6378–6382; as well as U.S. Pat. Nos. 5,223,409, 5,198,346, and 5,096,815).

A wide range of techniques are known in the art for screening gene products of combinatorial libraries made by point mutations, and, for that matter, for screening cDNA libraries for gene products having a certain property. Such techniques will be generally adaptable for rapid screening of the gene libraries generated by the combinatorial mutagenesis of CCR homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, the candidate combinatorial gene products are displayed on the surface of a cell, and the ability of particular cells or viral particles to bind a CDK, such as CDK4 or CDK6, via this gene product is detected in a "panning assay". For instance, the gene library can be cloned into the gene for a surface membrane protein of a bacterial cell (Ladner et al., WO 88/06630; Fuchs et al. (1991) *Bio/Technology* 9:1370–1371; and Goward et al. (1992) *TIBS* 18:136–140), and the resulting fusion protein detected by panning, e.g. using a fluorescently labeled molecule which binds the CCR-protein, e.g. FITC-CDK4, to score for potentially functional CCR homologs. Cells can be visually inspected and separated under a fluorescence microscope, or, where the morphology of the cell permits, separated by a fluorescence-activated cell sorter.

In similar fashion, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks. et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27-9400-01) can be easily modified for use in expressing and screening CCR combinatorial libraries of the present invention. For instance, the pCANTAB 5 phagemid of the RPAS kit contains the gene which encodes the phage gIII coat protein. The CCR combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate CCR-gene insert. The resulting recombinant phage contain phagemid DNA encoding a specific candidate CCR-protein, and display one or more copies of the corresponding fusion coat protein. The phage-displayed candidate proteins which are capable of, for example, binding a CDK, are selected or enriched by panning. For instance, the phage library can be panned on glutathione immobilized CDK-GST fusion proteins, and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for CCR homologs, e.g. p16, p15 or p13.5 homologs, which can then be screened for further biological activities in order to differentiate agonists and antagonists. Subsequent selection, e.g. of a reduced set of variants from the library, may then be based upon more meaningful criteria rather than simple CDK-binding ability. For instance, intracellular half-life or inhibitory potency can become selection criteria in secondary screens.

In light of the present disclosure, other forms of mutagenesis generally applicable will be apparent to those skilled in the art in addition to the aforementioned combinatorial mutagenesis. For example, p16, p15 or p13.5 homologs (both agonist and antagonist forms) can be generated and screened using, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32–34).

Consequently, the invention also provides for reduction of the subject CCR-proteins to generate mimetics, e.g. peptide or non-peptide agents, which are able to mimic binding of the authentic CCR protein to a cyclin dependent kinase, e.g. CDK4 and/or CDK6. Such mutagenic techniques as described above, as well as the thioredoxin system, are also particularly useful for mapping the determinants of a CCR-protein which participate in protein-protein interactions involved in, for example, binding of the subject CCR-protein to a CDK. To illustrate, the critical residues of a subject CCR-protein which are involved in molecular recognition of CDK4 can be determined and used to generate CCR-derived peptidomimetics which bind to CDK4 or CDK6 and, like the authentic CCR-protein, inhibit acitvation of the kinase. By employing, for example, scanning mutagenesis to map the amino acid residues of a particular CCR-protein involved in binding a cyclin dependent kinase, peptidomimetic compounds (e.g. diazepine or isoquinoline derivatives) can be generated which mimic those residues in binding to the kinase. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

In similar fashion, identification of mutations in CDK4 and/or CDK6 which effect binding to a CCR-protein can be used to identify potential peptidyl fragments of CDK4/CDK6 which can competitively bind a CCR-protein and interfere with its ability to inhibit the CDK. As describe below, we have characterized a CDK4 mutant which abrogates binding by p15 and p16, and consequently becomes insensitive to inhibition by those CCR-proteins. This mutation, in fact, occurs in a stretch of amino acid residues which is conserved between CDK4 and CDK6. Accordingly, peptidomimetics based on this stretch might be useful as antagonists of CCR-proteins, in that they are expected to compete with CDK4 or CDK6 for binding to the CCR-protein. In a preferred embodiment, the CCR anatagonist is a peptide or non-peptide analog of the amino acid sequence VAEIG(V/E)GAYG(T/K)V(F/Y)KARD, though more preferably a peptidomimetic of the amino acid sequence V(F/Y)KARD, and even more preferably of the tetrapeptide KARD. These and other peptidyl portions of CDKs can be tested for binding to CCR-proteins such as p15 or p16 using, for example, the thioredoxin fusion proteins constructs mention above.

Another aspect of the invention pertains to an antibody specifically reactive with one of the subject CCR-proteins. For example, by using peptides based on the cDNA sequence of the subject p16 protein, anti-p16 antisera or anti-p16 monoclonal antibodies can be made using standard methods. Likewise, anti-p13.5 and anti-p15 antibodies can be generated. A mammal such as a mouse, a hamster or rabbit can be immunized with an immunogenic form of the peptide (e.g., an antigenic fragment which is capable of eliciting an antibody response). Techniques for conferring immunogenicity on a protein or peptide include conjugation to carriers or other techniques well known in the art. For instance, a peptidyl portion of the protein represented by one of SEQ ID No. 2, 4 or 6 can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-CCR antisera can be obtained and, if desired, polyclonal anti-CCR antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495–497), as the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy,* Alan R. Liss, Inc. pp. 77–96). Hybridoma cells can be screened immunochemically for production of antibodies specifically reactive with the CCR-protein of interest and the monoclonal antibodies isolated.

The term antibody as used herein is intended to include fragments thereof which are also specifically reactive with a CCR-protein, e.g. anti-p16, anti-p15 or anti-p13.5 antibodies. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules.

Both monoclonal and polyclonal antibodies (Ab) directed against the subject CCR-proteins, and antibody fragments such as Fab' and F(ab')$_2$, can be used to block the action of particular CCR and allow the study of the cell-cycle or cell proliferation.

One application of anti-CCR antibodies is in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a CCR-protein, such as proteins antigenically related to p16, p15 or p13.5, can then be detected with antibodies, as, for example, reacting nitrocellulose filters lifted from infected plates with an anti-CCR antibody. Phage, scored by this assay, can then be isolated from the infected plate. Thus, the presence of CCR homologs, such as p16, p15 or p13.5 homologs, can be detected and cloned from other sources.

Antibodies which are specifically immunoreactive with one or more CCR-proteins of the present invention can also be used in immunohistochemical staining of tissue samples in order to evaluate the abundance and pattern of expression of the CCR-protein family, or particular members thereof. Anti-CCR antibodies can be used diagnostically in immunoprecipitation and immuno-blotting to detect and evaluate levels of one or more CCR-proteins in tissue or cells isolated from a bodily fluid as part of a clinical testing procedure. For instance, such measurements can be useful in predictive valuations of the onset or progression of tumors. Likewise, the ability to monitor certain CCR-protein levels in an individual can allow determination of the efficacy of a given treatment regimen for an individual afflicted with such a disorder. Diagnostic assays using anti-CCR antibodies, such as anti-p16 or anti-p15 antibodies, can include, for example, immunoassays designed to aid in early diagnosis of a neoplastic or hyperplastic disorder, e.g. the presence of cancerous cells in the sample, e.g. to detect-cells in which a lesion of a CCR-gene has occurred.

In addition, nucleotide probes can be generated from the cloned sequence of the subject CCR-proteins, which allow for histological screening of intact tissue and tissue samples for the presence of a CCR-protein encoding mRNA. Similar to the diagnostic uses of anti-CCR-protein antibodies, the use of probes directed to CCR-protein encoding mRNAs, or to genomic CCR-gene sequences, can be used for both predictive and therapeutic evaluation of allelic mutations which might be manifest in, for example, neoplastic or hyperplastic disorders (e.g. unwanted cell growth). Used in conjunction with anti-CCR protein antibody immunoassays, the nucleotide probes can help facilitate the determination of the molecular basis for a developmental disorder which may involve some abnormality associated with expression (or lack thereof) of a CCR-protein. For instance, variation in CCR-protein synthesis can be differentiated from a mutation in the coding sequence.

Accordingly, the present method provides a method for determining if a subject is at risk for a disorder characterized by unwanted cell proliferation. In preferred embodiments, method can be generally characterized as comprising detecting, in a tissue of said subject, the presence or absence of a genetic lesion characterized by at least one of (i) a mutation of a gene encoding a CCR-protein, such as p16, p15 or p13.5 or (ii) the mis-expression of the CCR-gene. To illustrate, such genetic lesions can be detected by ascertaining the existence of at least one of (i) a deletion of one or more nucleotides from a CCR-gene, (ii) an addition of one or more nucleotides to a CCR-gene, (iii) a substitution of one or more nucleotides of a CCR-gene, (iv) a gross chromosomal rearrangement of a CCR-gene, (v) a gross alteration in the level of a messanger RNA transcript of a CCR-gene, (vi) the presence of a non-wild type splicing pattern of a messanger RNA transcript of a CCR-gene, and (vii) a non-wild type level of a CCR-protein. In one aspect of the invention, there is provided a probe/primer comprising an oligonucleotide containing a region of nucleotide sequence which is capable of hybridizing to a sense or antisense sequence of any of SEQ ID Nos: 1, 3 or 5 or naturally occurring mutants thereof, or 5' or 3' flanking sequences or intronic sequences naturally associated with the subject CCR-genes or naturally occurring mutants thereof. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g. U.S. Pat. Nos. 4,683,195 and 4,683,202), or, alternatively, in a ligation chain reaction (LCR) (see, e.g., Landegran et al. (1988) Science 241:1077–1080; and Nakazawa et al. (1944) PNAS 91:360–364), the later of which can be particularly useful for detecting point mutations in the CCR-gene. Alternatively, the level of CCR-protein can detected in an immunoassay.

Moreover, the use of anti-sense techniques (e.g. microinjection of antisense molecules, or transfection with plasmids whose transcripts are anti-sense with regard to a certain CCR mRNA) can be used to investigate role of particular CCR-proteins, e.g. p16, p15 or p13.5, in the cell-cycle and cell proliferation, in a controlled environment, by inhibiting endogenous production of the protein. Such techniques can be utilized in cell culture, but can also be used in the creation of transgenic animals.

Another aspect of the invention features transgenic non-human animals which express a heterologous CCR-gene of the present invention, or which have had one or more genomic CCR-gene(s), disrupted in at least one of the tissue or cell-types of the animal. For instance, transgenic mice which have been disrupted at their p13.5 gene locus are described in Example 5.

In another aspect, the invention features an animal model for developmental diseases, which has a CCR allele which is mis-expressed. For example, a mouse can be bred which has a p16 or p15 allele deleted, or in which all or part of one or more p16 exons are deleted. Such a mouse model can then be used to study disorders arising from mis-expressed p16 genes.

Another aspect of the present invention concerns transgenic animals which are comprised of cells (of that animal) which contain a transgene of the present invention and which preferably (though optionally) express an exogenous CCR-protein in one or more cells in the animal. The CCR-transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosiac expression of the subject proteins can be essential for many forms of lineage analysis and can additionally provide a means to assess the effects of, for example, lack of p16 and p15 inhibition of CDKs which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject CCR polypeptide. For example, excision of a target sequence which interferes with the expression of a recombinent CCR-gene can be designed to activate expression of that gene. This interference with expression of the protein can result from a variety of mechanisms, such as spatial separation of the CCR-gene from the promoter element or an internal stop codon. Moreover, the transgene can be made wherein the coding sequence of the gene is flanked recombinance recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of Saccharomyces cerevisiae (O'Gorman et al. (1991) Science 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the CCR protein can be regulated via regulation of recombinase expression.

Use of the cre/loxP recombinase system to regulate expression of a recombinant CCR protein, such as p15 or p16, requires the construction of a transgenic animal containing transgenes encoding both the Cre recombinase and the subject protein. Animals containing both the Cre recombinase and the recombinant CCR genes can be provided through the construction of "double" transgenic animals. A convenient method for providing such animals is to mate two transgenic animals each containing a transgene, e.g., the CCR-gene and recombinase gene.

One advantage derived from initially constructing transgenic animals containing a CCR-transgene in a recombinase-mediated expressible format derives from the likelihood that the subject protein will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic p15 transgene is silent will allow the study of progeney from that founder in which diruption of cell cycle regulation by p15 in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the CCR-transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1-2p1 of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a CCR-gene can be controlled as above.

Yet another aspect of the invention pertains to methods of treating proliferative and/or differentiative disorders which arise from cells which, despite aberrant growth control, still require CDK4 or CDK6 for cell growth. There are a wide variety of pathological cell proliferative conditions for which the CCR-gene constructs and CCR-mimetics of the present invention can provide therapeutic benefits, with the general strategy being the inhibition of an anomalous cell proliferation. For instance, the gene constructs of the present invention can be used as a part of a gene therapy protocol, such as to reconstitute the function of a CCR-protein, e.g. p16, p15 or p13.5, in a cell in which the protein is misexpressed or in which signal transduction pathways upstream of the CCR-protein are dysfunctional. To illustrate, cell types which exhibit pathological or abnormal growth presumably dependent at least in part on a function of a CCR-protein include various cancers and leukemias, psoriasis, bone diseases, fibroproliferative disorders such as involving connective tissues, atherosclerosis and other smooth muscle proliferative disorders, as well as chronic inflammation. In addition to proliferative disorders, the treatment of differentiative disorders which result from, for example, de-differentiation of tissue which may (optionally) be accompanied by abortive reeentry into mitosis. Such degenerative disorders include chronic neurodegenerative diseases of the nervous system, including Alzheimer's disease, Parkinson's disease, Huntington's chorea, arylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors. It will also be apparent that, by transient use of gene therapy constructs of the subject CCR proteins (e.g. agonist and antagonist forms), in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For instance, CCR agonists and antagonists can be employed therapeutically to regulate organs after physical, chemical or pathological insult. For example, gene therapy can be utilized in liver repair subsequent to a partial hepatectomy, or to promote regeneration of lung tissue in the treatment of emphysema.

For instance, as described in the Examples below, transformation of a cell can be due in part to a loss-of-function mutation to a particular CCR-gene, e.g., ranging from a point mutation to gross deletion of the gene. Additionally, other data provided in the appended examples suggests that disorders suceptible to treatment with CCR agonists include those arising from cells which have lost the ability to induce CCR-protein expression. Normal cell proliferation, for instance, is generally marked by responsiveness to negative autocrine or paracrine growth regulators, such as members of the TGF-β family, e.g. TGF-β1, TGF-β2 or TGF-β3, and related polypeptide growth inhibitors, e.g. activins, inhibins, Müllerian inhibiting substance, decapentaplegic, bone morphogenic factors, and vg1 (e.g. terminal differentiation inducers). Ordinarily, control of cellular proliferation by such growth regulators, particularly in epithelial and hemopoietic cells, is in the form of growth inhibition. This is generally accompanied by differentiation of the cell to a post-mitotic phenotype. However, it has been observed that a significant percentage of human cancers derived from these cells types display a reduced responsiveness to growth regulators such as TGF-β3. For instance, some tumors of colorectal, liver epithelial, and epidermal origin show reduced sensitivity and resistance to the growth-inhibitory effects of TGF-β as compared to their normal counterparts. In this context, a noteworthy characteristic of several retinoblastoma cell lines is the absence of detectable TGF-β receptors. Treatment of such tumors with CCR agonists (e.g. CCR-proteins delivered by gene therapy or CCR-mimetics) provides an opportunity to restore the function of the RB-mediated checkpoint.

However, it will be appreciated that the subject method can be used to inhibit proliferation of cells which, in general, are still reliant on cyclin dependent kinases active in $G_1$, e.g. CDK4 or CDK6, irrespective of involvement of RB or RB-like proteins.

In accordance with the subject method, expression constructs of the subject CCR-proteins may be administered in any biologically effective carrier, e.g. any formulation or composition capable of effectively transfecting cells in vivo with a recombinant CCR-gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject CCR-proteins, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject CCR-genes, it is important to note that a prerequisite for the successful infection of target cells by most retroviruses, and therefore of stable introduction of the recombinant CCR-gene, is that the target cells must be dividing. In general, this requirement will not be a hindrance to use of retroviral vectors to deliver CCR-gene constructs. In fact, such limitation on infection can be beneficial in circumstances wherein the tissue (e.g. nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) PNAS 86:9079–9083; Julan et al. (1992) J. Gen Virol 73:3251–3255; and Goud et al. (1983) Virology 163:251–254); or coupling cell surface ligands to the viral env proteins (Neda et al. (1991) J Biol Chem 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the CCR-gene of the retroviral vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al. (1988) BioTechniques 6:616; Rosenfeld et al. (1991) Science 252:431–434; and Rosenfeld et al. (1992) Cell 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al. (1992) cited supra), endothelial cells (Lemarchand et al. (1992) Proc. Natl. Acad Sci. USA 89:6482–6486), hepatocytes (Herz and Gerard (1993) Proc. Natl. Acad. Sci. USA 90:2812–2816) and muscle cells (Quantin et al. (1992) Proc. Natl. Acad. Sci. USA 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7. pp. 109–127). Expression of the inserted CCR-gene can be under control of, for example, the E1A promoter, the major late promoter (MLP) and associated leader sequences, the E3 promoter, or exogenously added promoter sequences.

Yet another viral vector system useful for delivery of the subject CCR-gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

Other viral vector systems that may have application in gene therapy have been derived from herpes virus, vaccinia virus, and several RNA viruses. In particular, herpes virus vectors may provide a unique strategy for persistence of the recombinant CCR-gene in cells of the central nervous system and occular tissue (Pepose et al. (1994) Invest Ophthalmol Vis Sci 35:2662–2666)

In addition to viral transfer methods, such as those illustrated above, non-viral methods can also be employed to cause expression of a CCR-protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject CCR-gene by the targeted cell. Exemplary gene delivery systems of this type include liposomal derived systems, poly-lysine conjugates, and artificial viral envelopes.

In a representative embodiment, a gene encoding one of the subject CCR-proteins can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al. (1992) *Neurol. Med. Chir.* 32:873–876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, the subject CCR-gene construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via—mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) *Science* 260–926; Wagner et al. (1992) *PNAS* 89:7934; and Christiano et al. (1993) *PNAS* 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al (1994) *PNAS* 91: 3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical & Dental Materials*, ed. by David Williams (MIT Press: Cambridge, Mass., 1990); and the Sabel et al. U.S. Pat. No. 4,883,666. In another embodiment of an implant, a source of cells producing a the recombinant virus is encapsulated in implantable hollow fibers. Such fibers can be pre-spun and subsequently loaded with the viral source (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J. Biomech. Eng.* 113:178–183), or can be co-extruded with a polymer which acts to form a polymeric coat about the viral packaging cells (Lim U.S. Pat. No. 4,391,909; Sefton U.S. Pat. No. 4,353,888; Sugamori et al. (1989) *Trans. Am. Artif. Intern. Organs* 35:791–799; Sefton et al. (1987) *Biotechnol. Bioeng.* 29:1135–1143; and Aebischer et al. (1991) *Biomaterials* 12:50–55). Again, manipulation of the polymer can be carried out to provide for optimal release of viral particles.

To further illustrate the use of the subject method, the therapeutic application of a CCR-gene, e.g., by gene therapy, can be used in the treatment of a neuroglioma. Gliomas account for 40–50% of intracranial tumors at all ages of life. Despite the increasing use of radiotherapy, chemotherapy, and sometimes immunotherapy after surgery for malignant glioma, the mortality and morbidity rates have not substantially improved. However, there is increasing experimental and clinical evidence that for a significant number of gliomas, loss of TGF-$\beta$ responsiveness is an important event in the loss of growth control. Irrespective of the cause of decreased responsiveness, e.g. the loss of function of p15 or the loss of other TGF-$\beta$ signal transduction proteins, exogenous expression of p15 (or other CCR-protein) in the cell can used effectively to inhibit cell proliferation.

It has been demonstrated that gene therapy can be used to target glioma cells for expression of recombinant proteins (Miyao et al. (1993) *J. Neurosci. Res.* 36:472–479; Chen et al. (1994) PNAS 91:3054–3057; and Takamiya et al. (1993) *J. Neurosurg.* 79:104–110). Thus, a gene construct for expressing a CCR-protein can be delivered to the tumor, preferably by sterotactic-dependent means. In preferred embodiments, the gene delivery system is a retroviral vector. Since rapidly growing normal cells are rare in the adult CNS, glioma cells can be specifically transduced with a recombinant retrovirus. For example, the retroviral particle can be delivered into the tumor cavity through an Ommaya tube after surgery, or alternatively, packaging fibroblasts encapsulated in retrievable immunoisolatory vehicles can be introduced into the tumor cavity. In order to increase the effectiveness and decrease the side effects of the retrovirus-mediated gene therapy, glioma-specific promoters can be used to regulate expression of the CCR-gene. For example, the promoter regions of glial fibrillary acidic protein (GFAP) and myelin basis protein (MBP) can operably linked to the recombinant gene in order to direct glial cell-specific expression of the recombinant gene construct.

In another embodiment, gene therapy can be used in conjunction with the subject CCR-protein in the treatment of various carcinomas. Among the carcinomas, a strong correlation has been oberved between TGF-β responsiveness and both increasing malignant tumor grade and increasing proliferating cell nuclear antigen index (Coffery et al. (1988) *Cancer Res* 48:1596–1602; Masui et al. (1986) *PNAS* 83:2438–2442; and Knabble et al. (1987) *Cell* 48:417–428). In a representative embodiment, a gene therapy system comprising the subject CCR-gene in a retroviral vector is used to treat certain breast cancers. In preferred embodiments, expression of the subject CCR-protein-gene is controlled at least in part by a mammary-specific promoter, a number of which are available (for review, see Hennighausen (1990) *Protein Expression and Purification* 1:3–8; and Günzberg et al. (1992) *Biochem J* 283:625–632).

In similar fashion, gene therapy protocols involving delivery of the subject CCR-gene can be used in the treatment of malignant melanoma, which also serves as a model for progressive TGF-β resistance in transformation. In preferred embodiments, gene therapy protocols for treatment of melanomas include, in addition to the delivery of the CCR-gene construct by retroviral delivery, the delivery of a pharmaceutical preparation of the gene by direct injection. For instance, U.S. Pat. No. 5,318,514 describes an applicator for the electroporation of genes into epidermal cells and can be used in accordance with the present invention.

The subject CCR-gene constructs can be used in the treatment of hyperproliferative vascular disorders, e.g. smooth muscle hyperplasia (such as atherosclerosis) or restinosis, as well as other disorders characterized by fibrosis, e.g. rheumatoid arthritis, insulin dependent diabetes mellitus, glomerulonephritis, cirrhosis, and scleroderma, particularly proliferative disorders in which loss of TGF-β autocrine or paracrine signalling is implicated.

For example, restinosis continues to limit the efficacy of coronary angioplasty despite various mechanical and pharmaceutical interventions that have been employed. An important mechanism involved in normal control of intimal proliferation of smooth muscle cells appears to be the induction of autocrine and paracrine TGF-β inhibitory loops in the smooth muscle cells (Scott-Burden et al. (1994) *Tex Heart Inst J* 21:91–97; Graiger et al. (1993) *Cardiovasc Res* 27:2238–2247; and Grainger et al. (1993) *Biochem J* 294:109–112). Loss of sensitivity to TGF-β, or alternatively, the overriding of this inhibitory stimulus such as by PDGF autostimulation, can be a contributory factor to abnormal smooth muscle proliferation in restinosis. It may therefore be possible to treat or prevent restinosis by the use of gene therapy with CCR-gene constructs of the present invention. The CCR-gene construct can be delivered, for example, by percutaneous transluminal gene transfer (Mazur et al. (1994) *Tex Heart Inst J* 21:104–111) using viral or liposomal delivery compositions. An exemplary adenovirus-mediated gene transfer technique and compositions for treatment of cardiac or vascular smooth muscle is provided in PCT publication WO 94/11506.

Transforming growth factor-β is also understood to play a significant role in local glomerular and interstitial sites in human kidney development and disease. Consequently, the subject method provides a method of treating or inhibiting glomerulopathies and other renal proliferative disorders comprising the in vivo delivery and recombinant expression of the subject CCR-protein in kidney tissue.

The subject method can also be used to treat retinoblastomas in which the retinoblastoma gene (RB) is not itself impaired, e.g. the effective impairment of the RB checkpoint is the result of a failure to control CDK4 phosphorylation of RB. Thus, an exogenous CCR-gene can be expressed in a retinoblastoma cell, thereby causing inhibition of CDK4 activation and down-regulating RB phosphorylation. To illustrate, a recombinant retrovirus can be constructed to facilitate expression of p16 or p15, and infectivity of retinoblastoma cells enhanced by derivatizing the env protein with antibodies specific for retinoblastoma cells, e.g. antibodies to retinal S-antigen (Doroso et al. (1985) *Invest Opthalmol Vis Sci* 26:560–572; see also Liao et al. (1981) *Eur J Immunol* 11:450–454; and U.S. Pat. No. 4,444,744).

In yet another embodiment, the subject CCR-gene is delivered to a sarcoma, e.g. an osteosarcoma or Kaposi's sarcoma. In a representative embodiment, the gene is provided in a viral vector and delivered by way of a viral particle which has been derivatized with antibodies immunoselective for an osteosarcoma cell (see, for example, U.S. Pat. Nos. 4,564,517 and 4,444,744; and Singh et al. (1976) *Cancer Res* 36:4130–4136).

In a still further embodiment, the subject CCR-gene is recombinantly expressed in tissue which is characterized by unwanted de-differentiation and which may also be undergoing unwanted apoptosis. For instance, many neurological disorders are associated with degeneration of discrete populations of neuronal elements. For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Many are age-related, occurring in far greater incidence in older people than in younger. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Accordingly, the subject CCR-gene can be delivered to the effected tissue by gene therapy techniques. It is noted that numerous advances have been made in the construction of expression vectors, cellular and viral transgene carriers, and the characterization of target cells for neuronal gene therapy, and can be readily adapted for delivery of the subject CCR-genes (see, for example, Suhr et al. (1993) *Arch Neurol* 50:1252–1268; Jiao et al. (1993) *Nature* 362:450–453; Friedmann (1992) *Ann Med* 24:411–417; and Freese et al. (1991) *Nuc Acid Res* 19:7219–7223). In addition to degenerative-induced dementias, the subject gene therapy systems can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. Moreover, the use of CCR gene therapy constructs is ammenable to the treatment of disorders of the cerebellum which result in hypotonia or ataxia, such as those lesions in the cerebellum which produce disorders in the limbs ipsilateral to the lesion. For instance, p16 or p15 gene constructs can used to treat a restricted form of cerebellar corical degeneration involving the anterior lobes (vermis and leg areas) such as is common in alcoholic patients.

Furthermore, the subject CCR-genes can also be used in the treatment of autonomic disorders of the peripheral nervous system, which include disorders affecting the innervation of smooth muscle and endocrine tissue (such as glandular tissue). For instance, recombinant p16 or p15 expression by gene thereaopy can be used to treat tachycardia or atrial cardiac arrythmias which may arise from a degenerative condition of the nerves innervating the striated muscle of the heart.

Yet another aspect of the invention pertains to CDK4 and CDK6 mutants which are insensitive to the inhibitory control of one or more of the subject CCR proteins. With respect to cell cycle control, these mutants antagonize the action of CCR-proteins, and in preferred embodiments, are dominant negative mutants in that they remove from the control of mitosis certain cell-cycle checkpoints, such as checkpoints mediated by RB or RB-like proteins. Exemplary CDK4 and CDK6 mutants are represented in SEQ ID Nos. 9 (CDK4) and SEQ ID Nos. 10 (CDK6), wherein Xaa, which is an Arg in the wild-type enzyme, is mutated to render the enzyme insensitive to inhibition by CCR proteins. In preferred embodiments, Xaa is an amino acid other than arginine, though more preferably an amino acid which does not have a basic sidechain (e.g. not Arg, Lys or His). In a preferred embodiment, the Arginine is changed to a Cysteine.

The mutant CDK4 and CDK6 proteins, genes encoding such proteins, and antibodies specific for such proteins, can be provided in a manner analogous to any of the embodiments described above for each of the CCR-proteins. For instance, nucleic acids encoding the mutant kinases can be provided in any of a number of forms, e.g. as recombinant expression vectors as well as probes. Both isolated and recombinant forms of the enzymes are specifically contemplated, as well as antibodies which specifically bind the mutant forms of each of the kinases. Moreover, it will be appreciated that, whereever the present application mentions the utility for CCR antagonists, the subject CDK mutants can be utilized.

While the Arg→Cys mutant of CDK4 was first discovered in cells from a melanoma patient (see Example 10), mutagenic techniques such as those described above can be utilized to isolate yet other CDK4 and CDK6 mutants which are resistant to CCR protein inhibition. For instance, scanning mutagenesis or random mutagenesis can be used to generate a library of CDK mutants which can be screened for dominant negative mutations employing assays sensitive to CDK4 or CDK6 inhibition. For example, a library of CDK4 mutants can be transfected into cells which overexpress p16 and which are quiescent as a result. In the absence of mutations which uncouple the CDK4 mutant from p16/p15, the cell will remain quiescent. In constrast, mutations to the kinase which uncouple its activity from p16 will result in proliferation of cells expressing that mutant of CDK4. In a similar embodiment, the level of phosphorylated RB can be used to detect dominant negative mutants of CDK4, such as by immunodetection of phosphorylated RB, or the use of RB-sensitive reproter constructs the expression of which is dependent on the phosphorylation state of RB (e.g., see Park et al. (1994) *J Biol Chem* 269:6083–6088; Ouellette et al. (1992) *Oncogene* 7:1075–1081; and Slack et al. (1993) *Oncogene* 8:1585–1591). Mutants which uncouple p16/p15 inhibition of CDK4 will cause higher levels of phosphorylated RB protein to accumulate in the cell.

Exemplification

The invention now being generally described, it will be more readily understood by reference to the following examples which are included merely for purposes of illustration of certain aspects and embodiments of the present invention, and are not intended to limit the invention.

As described previously (see U.S. patent applications Ser. Nos. 08/154,915, 07/991,997 and 07/963,308, as well as Xiong et al. (1993) *Nature* 366:701; Xiong et al. (1993) *Genes Dev* 7:1572; Xiong et al. (1992) *Cell* 71:505; and Zhang et al. (1993) *Mol Cell Biol* 4:897), immunological procedures have been used to establish that cyclins associate, in eukaryotic cells, with a variety of potential catalytic subunits (e.g., CDKs, such as CDK2, CDK4 and CDK5). To illustrate, human cyclin D1 has been associated with a wide variety of proliferative diseases. In human diploid cells, specifically human diploid fibroblasts, cyclin D1 is complexed with a number of other cellular proteins. Among them are the catalytic subunits CDK2, CDK4 (previously called PSK-J3), CDK5 (also called PSSALRE), and CDK6 (PLSTIRE). In addition, polypeptides of 21 kDa and 36 kDa were identified in association with cyclin D1. It was shown that the 36 kDa protein is the Proliferating Cell Nuclear Antigen, PCNA. PCNA has been described as an essential accessory factor to the delta polymerase, which is required for leading-strand DNA replication and DNA repair. Cyclin D3 was also found to associate with multiple protein kinases, p21 and PCNA. It was therefore proposed that there exists a quaternary complex of D type cyclins, CDK, PCNA and p21, and that many combinatorial variations (cyclin D1, D3 with CDK2, 4, 5 and 6) may assemble in vivo.

The importance of the quaternary complex is emphasized by the discovery that cellular transformation by DNA tumor viruses is associated with selective subunit rearrangement of the cyclin D complexes, as well as other cell-cycle complexes, including cyclin A, CDC2, CDK2, CDK4 and CDK5 complexes. In particular, introduction of SV40 DNA tumor virus or its oncogenic gene product large T antigen into normal human diploid fibroblasts (HDF) causes disruption of the association between cyclin D and PCNA, CDKs (such as CDK2, CDK4, CDK5 and CDK6) and p21. For example, after dissociation from cyclin D and p21, CDK4 kinase becomes associated with a 16 kDa polypeptide (p16). Similarly, SV40 transformation causes a decrease of association of p21 with cyclin A in HDF; and adenovirus-(293 cell line) or human papilloma virus-(HeLa cell line) transformed cells, p21 is completely disassociated from cyclin A. A 19 kDa peptide, p19, then appears in a complex with cyclin A.

Thus, in many transformed cells, cyclin and CDK's associate in binary complexes which form the core of the cell-cycle regulatory machinery. In normal cells, a major fraction of the cyclin kinases acquire two additional subunits (p21 and PCNA) and thereby form quaternary complexes. Reconstitution of quaternary complexes in insect cells revealed that p21 is a universal inhibitor of cyclin kinases. As such, p21 inhibits cell-cycle progression and cell proliferation upon overexpression in mammalian cells. Taken in conjunction with the previously demonstrated absence of p21 protein in the cell-cycle kinase complexes of cells with deficient p53, these results suggest that p21 is a transcriptional target of the tumor suppressor protein, p53. One function of p53 is to act in a cellular signaling pathway which causes cell-cycle arrest following DNA damage (see for example, Kastan et al. *Cell* 71:587–5971993). It has therefore been suggested that p21 forms a critical link between p53 and the cell-cycle control machinery.

Cyclin D/CDK4 kinase differs from the others in its inability to utilize histone H1 as a substrate. To date, the only substrates known for cyclin D/CDK4 kinases are the members of the RB family of "pocket" proteins (Matsushime et al., *Cell* 71:323–334 (1992)). Therefore, the effect of p21 was tested on the ability of cyclin D/CDK4 to phosphorylated RB. Insect cell lysates containing cyclin D or CDK4 alone showed little activity toward GST-RB. However, cyclin D/CDK4 binary complexes catalyzed substantial RB phosphorylation. Addition of increasing amounts of p21 resulted in the accumulation of cyclin D/CDK4/p21 ternary complexes with a corresponding inhibition of RB phosphorylation. Inclusion of PCNA was essentially without effect. However, cells lacking functional p53 may nevertheless retain a functional RB checkpoint which undergoes differential phosphorylation despite lack of endogneous p21.

The two-hybrid screening system (Fields et al. *Nature* 340:254 (1989)) was utilized to search for proteins that could interact with human CDK4, and more specifically, to isolate a cDNA encoding p16. Two-hybrid screening relies on reconstituting a functional GAL4 activator from two separated fusion proteins: the GAL4 DNA-binding domain fused to CDK4, GAL4db-CDK4; and the GAL4 activation domain fused to the proteins encoded by HeLa cDNAs, GAL4ad-cDNA. YPB2 was used as the recipient yeast as it is a strain that contains two chromosomal genes under the control of two different GAL4-dependent promoters: HIS3 and LacZ. YPB2 was transformed with a mixture of two plasmids encoding, respectively, the GAL4db-CDK4 and the GAL4ad-cDNA fusions; several clones were obtained that grew in the absence of histidine and that turned blue in the presence of β-gal. From DNA sequencing data it was determined that each of the positive clones derived from the same gene, although one group represented mRNAs with a shorter 3' end. The sequence of these cDNAs contained, in-phase with the GAL4ad, an open reading frame encoding a protein of 148 amino acids with a predicted molecular weight of 15,845 daltons (see SEQ ID Nos. 1 and 2). The sequence of p16 was compared by standard methods with those present in the currently available data banks and no significant homologies were found.

To test if p16 would specifically bind CDK4, YPB2 were cotransformed with the GAL4ad-p16 fusion as well as with several target GAL4db fusion constructs containing, respectively, cdc2, CDK2, CDK4, CDK5, PCNA and Snfl (a fission yeast kinase). Transformed cells were plated with and without histidine. Only the GAL4db-CDK4 fusion interacted with GAL4ad-p16 to an extent which allowed growth in the absence of histidine, indicating that this pair of fusion proteins specifically reconstituted a functional GAL4 activator able to enhance the expression of the HIS3 gene. The same result was obtained when the ability to transactivate the expression of the β-galactosidase gene was assayed.

The specificity of this interaction was further demonstrated in a cell-free system, by mixing in vitro translated ($^{35}$S)-labeled CDKs with a purified bacterially-produced fusion protein consisting of glutathione-S transferase (GST) linked to p16 (17). The GST-p16 fusion was recovered by binding to glutathione-sepharose beads and the association of each CDK was analyzed by gel electrophoresis. Consistent with the previous observations, GST-p16 bound much more efficiently to CDK4 than to cdc2, CDK2 or CDK5.

Since the predicted molecular weight of p16 is close to 16 Kd, the identity of p16 as the CDK4-associated p16 protein found in transformed cell lines (see above) was determined. Two in vitro translation products of 15 KD and 17 KD were obtained from the p16 cDNA. These products, as well as the CDK4-associated p16 protein from HeLa cells were treated with N-chlorosuccinimide. The partial NCS-proteolytic pattern of the 17 KD cDNA-derived product was very similar to the pattern obtained with the CDK4-associated p16 protein from HeLa cells, strongly suggesting that the p16 cDNA actually corresponds to p16. Partial digestion with V8 protease of the 17 KD cDNA-derived product and p16 also yielded similar patterns. It is interesting to note that the p16 protein overexpressed in insect cells has an electrophoretic mobility of 15 KD, and its NCS proteolytic map is identical to that obtained with the 15 KD cDNA derived product. This suggests that the actual p16 found in human cells and the 17 KD in vitro translation product correspond to posttranslationally modified proteins. The fact that the p16 protein overexpressed in insect cells interacts with CDK4 suggests that this modification is not essential for the interaction (see below).

The identity between p16 and the CDK4-associated protein p16 was further confirmed using antibodies raised against the purified GST-p16 fusion protein. Several human cell lines were used for this experiment: a normal cell line WI38, derived from normal lung fibroblasts; the VA13 cell line derived from WI38 by transformation with the SV40 T-antigen; and HeLa cells. As set out above, anti-CDK4 immunoprecipitates of WI38 revealed the association of CDK4 with cyclin D1, PCNA, p21 and p16. In contrast, in VA13 and HeLa cells CDK4 is only associated with p16. Anti-p16 immunoprecipitates contained a protein with an apparent molecular weight of 16 KD which was readily detectable in the two transformed cell lines, VA13 and HeLa but to a lesser extent in the normal cell line WI38. This protein not only had the same electrophoretic mobility as the p16 protein coimmunoprecipitated with anti-CDK4 serum, but also had an identical NCS partial proteolytic pattern. In addition to p16 a protein of 33 Kd was observed in anti-p16 coimmunoprecipitates that was shown to be identical to CDK4 by V8-proteolytic mapping.

Northern analysis of the transcripts present in WI38 and VA13 cells indicated that the p16 mRNA was around many times less abundant in WI38 cells compared to VA13 cells.

This difference approximately corresponded to the observed difference in the amount of p16 protein between the two cell lines, suggesting the possibility that p16 expression might be regulated at a transcriptional or post-transcriptional level. Indeed, in three non-virally transformed cell lines the expression of p16 could not be detected even after overexposure of the gel.

To study the biochemical consequences of the interaction of p16 with CDK4, active CDK4-cyclin D complexes have been reconstituted in vitro by standard protocols (Kato et al. *Genes Der* 7:331 (1993); and Ewen et al. *Cell* 73:487 (1993)). The three relevant components, CDK4, p16 and cyclin D1, were expressed in baculovirus-infected insect cells. Extracts were prepared from metabolically ($^{35}$S)-labeled insect cells that separately overexpressed p16, CDK4 or cyclin D1, as well as from cells overexpressing both CDK4 and cyclin D1. In response to increasing amounts of p16, corresponding decreases in the ability of CDK4 to phosphorylate RB was observed. This inhibition correlated with the association between p16 and CDK4 as detected by immunoprecipitation. No inhibition was observed when CDK2-cyclin D2 complexes were used in a similar assay. To confirm that the inhibition of CDK4 was due to p16, a His-tagged p16 fusion protein (His-p16) was created to have an amino terminal extension of 20 amino acids containing a tract of 6 histidine residues. This fusion protein was overexpressed in baculovirus-infected insect cells, and was purified by virtue of the high-affinity association of the histidine tract to nickel-agarose beads. The His-p16 protein preparation was shown to be >90% pure, and inhibited the activity of the CDK4-cyclin D1 complex under conditions similar to those used for inhibition by the whole lysates.

The role of the retinoblastoma gene product (RB), appears to be as a cell-cycle checkpoint which appears to at least act be sequestering transcription factors responsible for the proteins of phase. In many carcinomas, p53 function is lost by mutation or deletion. RB, on the other hand, is not apparently altered as often. However, because p16 down-regulates the CDK4/cyclin D complex, which acts to phosphorylate RB, it is proposed herein that p16 loss in certain carcinomas can alleviate the effects of the RB checkpoint and, in some manner of speaking, represent a checkpoint deficiency analogous to p53 loss. The loss of p16 would result in more effective phosphorylation of RB and hence would remove the RB-mediated inhibition of the cell-cycle. Consistent with this notion, it is described below that in a variety of human tumor cells, such as cells which over-express a D-type cyclin, e.g. cyclin D1 or D2, the p16 gene is lost from the cell, e.g. homozygously deleted.

Moreover, as described in the examples below, the p16 gene was found to map to the human region 9p21–22, a known melanoma locus (Walker et al. (1994) *Oncogene* 9:819; Coleman et al. (1994) *Cancer Res* 54:344; Cheng et al. (1993) *Cancer Res* 53:4761; and Cannon-Albright et al. (1992) *Science* 258:1148). The chromosomal mapping was further confirmed by analysis of somatic cell hybrids through PCR amplification (using primers ex1A and ex13 of FIG. 2A). Somatic hybrids containing human chromosome 9 resulted in positive PCR products being appllified.

Utilizing primers generated from the cDNA sequence of human p16 (SEQ ID No. 1) which are shown in FIG. 1, the genomic p16 gene was partially sequenced to determine intron/exon boundaries. The approximate sequences of the nucleic acid flanking Exon 1 and Exon 2 (see FIG. 1) are shown in FIGS. 2A and 2B and 3A–D respectively.

Genomic DNA was isolated from a variety of human tumor lines (Sambrook et al. *Molecular Cloning: A Laboratory Manual*, CSHL Press, Cold Spring Harbor, N.Y. (1989)) and was probed by PCR reactions for the presence or absence of p16 sequences. In particular, primers ex1A and ex13 (FIG. 2A) were used to score for exon 1 of p16, and primers ex14 and ex15 were likewise used to detect exon 2 of p16. As shown in FIG. 4, the p16 gene is disrupted in several tumor cell lines, confirming that p16 is indeed likely to be critical in cell transformation in certain cancerous cells. Moreover, probing of these cell lines with full length p16 cDNA (SEQ ID No. 1) demonstrated that in at least 3 of those cells apparently missing a portion of the p16 gene, the entire gene was in fact absent.

Based on immunoprecipitation experiments with anti-p16 antibodies, as well as oligonucleotide hybridization assays, it became apparent that the p16 protein represented by SEQ ID No. 2 is merely one member of a larger family of related cell-cycle regulatory proteins. For instance, even under high stringency conditions, Southern hybridation experiments of mRNA from different tissue types has indicated that approximately 4 closely related transcripts are produced. These p16 homologs, members of the CCR-protein family, may have arisen by gene duplication (e.g. each CCR-protein arises from a distinct gene) or from alternate exon splicing at the mRNA level, or a combination thereof.

Utilizing a probe consisting of the coding region of the human p16 gene, we have screened a mouse embryonal stem cell library and have isolated a genomic clone containing the coding region for a mouse homolog of the human p16 gene described above. This clone was isolated under low to moderate stringency conditions (1xSSC at 50° C.). This DNA (14 kB) has been cloned in two independent pieces and the restriction map for nine restriction endonucleases has been performed (see FIG. 5). The mouse CCR-gene has been completely sequenced and the coding region is apparently made up of only two exons that have been located in the restriction map by Southern hybridization. The apparent molecular weight of the mouse CCR-protein is 13.5 kDa, and the nucleic acid and amino acid sequence of the mouse CCR-protein, termed herein "p13.5", is given in SEQ ID No. 5 and 6 respectively.

Moreover, utilizing degenerate probes based on the most highly conserved sequences between the human p16 clone and mouse p13.5 clone (e.g. between residues Met-52 through Gly-135 of human p16 and Met-1 through Gly-83 of mouse p13.5), we have isolated a number of human p16 homologs.

In addition, it has been noted that TGF-β treatment causes accumulation of RB in the under-phosphorylated state and expression of RB-inactivating viral oncoproteins prevents TGF-β induced cell cycle arrest (Laiho et. al. (1990) *Cell* 62:175–185; and Pietenpol et al. (1990) *Cell* 61:777–785). While prior publicatiosn have suggested that TGF-β treatment results in down-regulation of CDK4 expression (Ewen et al. (1993) *Cell* 74:1009–1020), the data suggested to us that TGF-β might function through suppression of RB phosphorylation and pointed to the possibility that one result of TGF-β treatment might be inhibition of cyclin dependent kinases.

Accordingly, to investigate the mechanism by which TGF-β inhibits cell proliferation, we examined anti-CDK immunoprecipitates from human keratinocytes which had been arrested in G1 by exposure to TGF-β. Notably, immunoprecipitates of two G1-specific cyclin kinases, CDK4 and CDK6, contained several low molecular weight, associated proteins. These included p16 and two additional proteins of approx. 15 and 15.5 kDa. These proteins were not recovered in parallel CDC2 or CDK2 immunoprecipitates but were recovered in anti-p16 immunoprecipitates, suggesting that p15, p15.5 and p16 might be related. This was confirmed by western blotting of CDK4 and CDK6 immunoprecipitates which demonstrated that p15 and p15.5 were weakly cross-reactive with the p16 antiserum.

To isolate clones encoding putative p16 relatives, we constructed a cDNA library from TGF-β arrested HaCaT cells (Boukamp et al. (1988) *J Cell Biol* 106:761–771) and probed this library at low-stringency with the p16 coding sequence (SEQ ID No. 1). One clone obtained in this screen encoded a 137 amino acid protein (predicted M.W. 14.7 kDa.) with homology to p16. Based upon this homology and upon biochemical properties described below, we have named this protein p15. The first 50 amino acids of p15 and p16 share approx. 44% identity. This is followed by an 81 amino acid region of approx. 97% identity (see FIG. 6) after which p15 and p16 sequences diverge. The sequence of p15 can be divided into four ankyrin repeats suggesting that this structural motif is conserved in the CCR-protein family. In vitro translation of the p15 cDNA produced a protein which precisely comigrated with the p15 band present in CDK4, CDK6 and p16 immunoprecipitates from TGF-β arrested HaCaT cells. Identity of these proteins was confirmed by protease and chemical cleavage mapping.

To investigate the functional similarity of p15 and p16, we expressed p15 as a fusion protein in bacteria and tested its ability to bind and inhibit cyclin dependent kinases. p15 specifically bound CDK4 and CDK6 but did not appreciably bind CDC2, CDK2 or CDK5. To assess the consequences of binding, p15 was added to active cyclin/CDK complexes expressed in insect cells. p15 specifically inhibited the cyclin D/CDK4 and cyclin D/CDK6 enzymes but had no effect on CDK2/cyclin A kinase. Thus p15 is a functional member of the CCR-protein family. Moreover, FISH mapping of the p15 gene demonstrated that this gene lies adjacent to the p16 gene at 9p21.

While we first noted p15 in immunoprecipitates from HaCaT cells which had been arrested in G1 by serum starvation and re-stimulation in the presence of TGF-β, by comparison, we found that asynchronous, rapidly proliferating HaCaT cells contained considerably lower levels of p15 in CDK4 and CDK6 immunoprecipitates. To separate effects of TGF-β treatment from effects of G1 arrest, asynchronous cultures were treated with TGF-β for various periods, after which patterns of CDK4 and CDK6 associated proteins were examined. In as little as four hours following TGF-β addition, p15 levels rose in CDK4 and CDK6 immunoprecipitates, reaching peak levels after 6–8 hours. In contrast, CDK-associated p16 levels were unaffected by TGF-β. Northern blotting of RNA from cultures treated in parallel revealed that increased CDK4-associated p15 reflected increased abundance of p15 mRNA. In 2 hours following TGF-β treatment, p15 mRNA began to rise and reached a peak induction of approx. 30-fold after 6–8 hours. In contrast, p16 mRNA levels did not vary.

Two other mechanisms for TGF-β mediated cell cycle arrest have been previously proposed. In Mv1Lu cells, TGF-β treatment suppressed CDK4 synthesis. This was deemed causal since cells could be rendered resistant to TGF-β by constitutive overexpression of CDK4. In HaCaT cells, TGF-β treatment had no effect on CDK4 protein or mRNA levels. Based upon the properties of p15, we would predict that CDK4 overexpression could also render HaCaT cells TGF-β resistant by titrating the p15 CDK4/CDK6 inhibitor. p27, a CDK inhibitor which was purified from TGF-β arrested cells, has also been proposed as a link between TGF-β and cell cycle control. However, in HaCaT cells, TGF-β treatment had no effect on p27 mRNA levels. Thus any contribution that p27 may make to TGF-β mediated cell cycle arrest in these cells must occur by regulation at the post-translational level.

Considered together, our data suggest that p15 may function as an effector of TGF-β mediated cell cycle arrest via inhibition of CDK4 and CDK6 kinases. p15 may be the sole mediator of TGF-β induced arrest in some cells, or may cooperate with other TGF-β responsive pathways. TGF-β can regulate differentiation in some cell types, and the ability of TGF-β to affect cell cycle progression through p15 may also contribute to these processes.

Moreover, cytogenetic abnormalities at 9p21 are common in many types of human tumors suggesting the presence of a tumor suppressor gene at this locus. An inherited cancer syndrome which causes predisposition to melanoma also maps to 9p21. In addition to our data presented herein, and in U.S. Ser. Nos. 08/248,812 and in 08/227,371, p16 was initially proposed as a candidate for both of these activities based upon analysis of p16 deletions and point mutations in cell lines. However, the presence of a second functional member of the p16 family at 9p21 raises the possibility that loss of tumor suppression may involve inactivation of either or both genes. The response of p16 to viral oncoproteins indicates that it may function in intracellular growth regulaltory pathways, while results presented here suggest that p15 may transduce extacellular growth inhibitory signals. Thus deletions of 9p21 which remove both genes (or other mutations that might inactivate both) could simultaneously negate two major proliferative control pathways. In this regard, the ability of TGF-β to induce growth arrest is reduced or lost in many neoplastically transformed cell lines. In particular, melanocytes are sensitive to growth inhibition by TGF-β, but many metastatic melanoma cells are TGF-β resistant.

EXAMPLE 1

Demonstration of Selective Subunit Rearrangement of Cell-cycle Complexes In Association With Cellular Transformation by a DNA Tumor Virus or Its Oncogenic Product (i) Cellular Transformation With DNA Tumor Virus SV40 Is Associated With Subunits Rearrangement of Cell-cycle Complexes Preparation of [$^{35}$S] methionine-labelled cell lysates and polyacrylamide gel electrophoresis were as described above, as well as described in PCT Publication No. WO92/20796. Cell lysates were prepared from either human normal diploid fibroblast cells WI38 or DNA tumor virus SV40 transformed WI38 cells, VA13. Cell lysates were immunoprecipitated with antibodies against each cell-cycle gene products.

(ii) Subunit Rearrangements of Cell-cycle Complexes In Two Different Pair Cell Lines Methods for preparation of cell lysates are the same as described above. Two different pair cell lines were used in these experiments. HSF43 is a normal human diploid fibroblast cell line and CT10 (full name CT10-2C-T1) is a derivative of HSF43 transformed by SV40 large tumor antigen. CV-1 is an African green monkey kidney cell line and COS-1 is a derivative of CV-1 transformed by SV40.

(iii) Cellular Transformation by DNA Tumor Virus SV40 Is Associated With Rearrangement of PCNA Subunit of Cell-cycle Complexes Preparation of cell lysate, electrophoresis, and Western blotting conditions are the same as described above. Normal human diploid fibroblast cell lines and their SV40 transformed cell lines are described above. Immunoprecipitates derived from each antibody were separated on polyacrylamide gels and blotted with anti-PCNA antibody.

(iv) Cellular Transformation by DNA Tumor Virus SV40 Is Associated With Rearrangement of CDK4 Subunit of Cell-cycle Complexes Preparation of cell lysate, electrophoresis, and Western blotting conditions are the same as previously described. Normal human diploid fibroblast cell lines and their SV40 transformed cell lines are described above. Immunoprecipitates derived from each antibody were separated on polyacrylamide gels and blotted with anti-CDK4 antibody.

EXAMPLE 2

Cloning of p16, an Inhibitor of CDK4 Activity (i) Cloning of p16 using the two hybrid assay

*Saccharomyces cerevisiae* YPB2 cells were transformed simultaneously with a plasmid containing a GAL4db-p16 fusion and with a plasmid containing, respectively, the GAL4ad fused to cdc2 (CDK1), CDK2, CDK4, CDK5, PCNA (proliferating cell nuclear antigen), and the fission yeast kinase Snf 1. After growing cells in medium selective for both plasmids (minus tryptophan and minus leucine), two colonies were picked randomly and were streaked in plates that either contained or lacked histidine. The ability to grow in the absence of histidine depends on the expression of the HIS3 gene that is under a GAL4-responsive promoter and, therefore, indicates that a functional GAL4 activator has been reconstituted through the interaction of p16 with the corresponding target protein.

(ii) Interaction of p16 CDKs

Purified bacterially-produced GSTp16 fusion protein was mixed with ($^{35}$S)-labeled in vitro translated cdc2, CDK2, CDK4 and CDK5. Mixtures contained 0.5 µg of purified GST-p16 and an equivalent amount of in vitro translated protein (between 0.5 to 5 µl; TNT Promega) in a final volume of 200 µl of a buffer containing 50 mM Tris-HCl pH 8, 120 mM NaCl and 0.5% Nonidet P-40. After 1 h at 4° C., 15 µl of glutathione-agarose beads were added and incubation was resumed for an additional hour. Beads were recovered by centrifugation, washed 4 times with the incubation buffer, and mixed with standard protein-gel loading buffer. Samples were loaded into a 15% poly-acryllamide gel and ($^{35}$S)-labeled proteins were detected by fluorography. The GSTp16 fusion protein was overexpressed in the pGEX-KG vector and purified by standard techniques. The in vitro translation templates were derived from the pBluescript vector (Stratagene).

(iii) Proteolytic mapping of p16

The in vitro translated ($^{35}$S)-labeled p16 (TNT Promega) was obtained using the p16 cDNA cloned into pBluescript vector (Stratagene) as a template, and the CDK4-associated p16 protein was co-immunoprecipitated with an anti-CDK4 serum from metabolically ($^{35}$S)-labeled HeLa cells lysates. Partial proteolysis was done over the corresponding gel slices after extensive equilibration in a buffer and digestion was accomplished by addition of NCS at different concentrations. The products were run in a 17.5% polyacrilamide gel and detected in a phosphoimager Fujix 2000.

(iv) Detecting the effects of p16 on CDK4-cyclin D complexes

Baculovirus-infected insect cells overexpressing p16, CDK4, cyclin D1, or both CDK4 and cyclin D1 together were metabolically ($^{35}$S)-labeled. The different incubation mixtures were composed by extracts containing p16, CDK4, cyclin D1 and both CDK4 and cyclin D1, and were immunoprecipitated with anti-p16 serum, anti-CDK4 serum without any previous preincubation, and anti-CDK serum preincubated with the peptide originally used to raise the antiserum and anti-cyclin D1 serum. Immunoprecipitates were then analyzed by SDS-PAGE.

EXAMPLE 3

Chromosomal Mapping of p16

Genomic clones of the human p16 gene were isolated by stringency screening (68° C. with 0.1×SSC wash) of a λFIXII human genomic library (Strategene) with cDNA probes. Isolated phage clones were confirmed by high stringency Southern hybridization and/or partial sequence analysis. Purified whole phage DNA was labelled for fluorescent in situ hybridization (FISH) analysis.

FISH analysis was performed using established methods (Demetrick et al. (1994) *Cytogenet Cell Genet* 66:72–74; Demetrick et al. (1993) *Genomics* 18:144–147; and DeMarini et al. (1991) *Environ Mol Mutagen* 18:222–223) on methotrexate or thymidine synchronized, phytohemagglutinin stimulated, normal peripheral blood lymphocytes. Suppression with a mixture of sonicated human DNA and cot1 DNA was required to reduce the background. The stained slides were counterstained with propidiem iodide (for an R banding pattern) or DAPI and actinomycin D (for a DA-DAPI banding pattern), mounted in antifade medium and visualized utilizing a Zeiss Axiphot microscope. Between 30 and 100 mitotises were examined for each gene location. Photographs were taken using a cooled CCD camera. Alignment of three color fluorescence was done under direct visualization through a triple bandpass filter (FITC/Texas Red/DAPI). The p16 gene was visualized to map to 9p21–22.

EXAMPLE 4

Cloning of Mouse CCR-proteins

Utilizing a probe consisting of the coding region of the human p16 gene, we have screened a mouse embryonal stem cell library and have isolated a genomic clone containing the coding region for a mouse homolog of the human p16 gene described above. This clone was isolated under low to moderate stringency conditions (1×SSC at 50° C.). This DNA (14 kB) has been cloned in two independent pieces and the restriction map for nine restriction endonucleases has been performed (see FIG. 5). The mouse CCR-gene has been completely sequenced and the coding region is apparently made up of only two exons that have been located in the restriction map by Southern hybridization. The apparent molecular weight of the nouse CCR-protein is 13.5 kDa, and the nucleic acid and amino acid sequence of the mouse p16 homolog, termed herein "p13.5", is given in SEQ ID No. 5 and 6 respectively.

Utilizing a probe based on the nucleotide sequence of the conserved region of Met1-Arg80 (see FIG. 6) of teh mouse p13.5 clone, a p19 embryonal carcinoma library (Stratagene) was probed under high stringency conditions. Several clones were isolated fro the library, some of which were seemingly identical to the p13.5 clone, and one which the partial sequence (SEQ ID Nos. 7 and 8) indicated that it was the murine homolog of either p16 or p15.

EXAMPLE 5

Cloning of p15 From Human Cells

The sequence of the p15 cDNA is shown along with the deduced amino acid sequence of the protein in SEQ ID Nos. 3 and 4 respectively. The deduced amino acid sequence of p15 wascompared to that of p16 (e.g. see FIG. 6), and areas of homology were identified using the BLAST program.

(i) Cell Culture

HaCaT cells were routinely maintained in DMEM containing 10% fetal bovine serum (FBS) ( Boukamp et al. (1988) *J Cell Biol.* 106:761–771). For TGF-β arrest, HaCaT cells were grown to confluence in DMEM containing 10% FBS (FBS) and then serum starved for 3 days in DMEM containing 0.1% FBS. Cells were re-stimulated by addition of new media containing 10% FBS and 2 ng/ml TGF-β (purified from human platelets, Calbiochem). For library construction, RNA was prepared 22 hours after re-stimulation. For immunoprecipitations experiments, cells were labelled with $^{35}$S-methionine in the presence of TGF-β for four hours beginning at 19 hours after re-stimulation.

(ii) Library Construction and Screening

RNA was prepared from TGF-β treated cells and from cells that were serum starved and then re-stimulated in the absence of TGF-β using RNAZOL B according to the manufacturer's instructions. The cDNA library which was used to isolate the p15 clone was constructed from a mixture of RNA derived from treated and untreated cells. Messenger RNA preparation and cDNA synthesis were exactly as previously described (Hannon et al. (1993) *Genes Dev.* 7:2378–2391). Double-stranded cDNA was ligated into λ-ZapII arms according to the manufacturers instructions. Low stringency hybridization was performed at 50° C. in 500 mM NaPO$_4$, pH 7.0, 1 mM EDTA, 15% Formamide, 7% SDS, 0.1% bovine serum albumin (wash: 1×SSC, 50° C.). The p15 cDNA was also isolated from a human mammary epithelial cell library. Cell lysis, immunoprecipitation and protease mapping were performed exactly as previously described (Xiong et al. (1993) *Nature* 366:701–704) For chymotrypsin digestion, either 7 μg or 1.5 μg of enzyme was used. Gels for chymotrypsin mapping contained 0.1% SDS.

EXAMPLE 6 p15 is a Specific Inhibitor of CDK4 and CDK6

Preparation of GST-p16 fusion protein from bacteria is described above. GST-p15 was prepared identically.

(i) p15 Binds CDK4 and CDK6

In vitro translated CDKs were prepared using the TNT-lysate in vitro translation kit (Promega) according to the manufacturer's instructions. For the binding assay, GST-p15 or GST-p16 (250 ng) was incubated with in vitro translated CDKs, e.g. $^{35}$S-labelled CDC2, CDK2, CDK4, CDK5 or CDK6, for 30 minutes at 30° C. in 30 μl containing 20 mM Tris, pH 8.0, 10 mM MgCl$_2$, 1 mM EGTA. Following incubation, mixtures were diluted to 250 μl in IP buffer (50 mM Tris, pH 8.0, 150 mM NaCl, 0.5% NP-40) and incubated for 1 hour with 12.5 μl of glutathione sepharose. Bound proteins were recovered on glutathione sepharose, washed four times with 1 ml of IP buffer, and then released by boiling in SDS gel sample buffer. Bound proteins were analyzed by electrophoresis in a 17.5% PAGE gel. For comparison, a similar experiment using GST-p16 was carried out.

(ii) p15 Binding Inhibits Cyclin D/CDK4 Kinase

Active cyclin D/CDK4 kinase, present in lysates of baculovirus infected insect cells, was incubated with increasing quantities of GST-p15 for 30 minutes at 30° C. Preparation of baculovirus lysates containing active cyclin D/CDK4 kinase is described above. Lysates containing active cyclin D/CDK6 were prepared identically. For kinase assays 10 μl of baculoviral lysates were mixed with approximately 0, 10 ng, 20 ng, 50 ng, or 100 ng of GST-p15 or GST-p16 and incubated for 30 minutes at 30° C. in a total volume of 30 μl containing 20 mM Tris, pH 8.0, 10 mM MgCl$_2$, 1 mM EGTA. Following incubation, 0.5 μg GST-RB and 0.5 μl of γ-$^{32}$P-ATP (5 μlCi, 3000 Ci/mMol) were added for 10 minutes at 30° C. as substrates. Reactions were stopped by the addition of 250 μl of IP buffer and 15 μl of glutathione sepharose. After a further 1 hour of incubation at 4° C., beads were washed four times with IP buffer before release of bound proteins and subsequent electrophoresis. Like p16, the p15-GST fusion protein was able to inhibit the kinase activity of CDK4.

(iii) p15 Inhibits Cyclin D/CDK6 Kinase

Cyclin D/CDK6 complexes were produced in baculovirus infected insect cells and incubated with increasing quantities of GST-p15 or GST-p16 as described above. Following incubation, the ability of these complexes to catalyze GST-RB phosphorylation was determined. Both p15 and p16 demonstrated an ability to inhibit the CDK6 kinase activity.

EXAMPLE 7

TGF-β Treatment Increases Association of p15 With CDK4 and CDK6

HaCaT cells were cultured as described above. TGF-β treatment was initiated by adding TGF-β to existing media to 2 ng/ml. For the last two hours of TGF-β treatment, cells were labelled with $^{35}$S-methionine. For cell labelling, media was changed to DMEM minus methionine (Gibco-BRL) containing 2 ng/ml of TGF-β, 10% dialyzed FBS and 0.5 mCi/ml of $^{35}$S-methionine/cysteine (trans-label, NEN). Cells were lysed and proteins were immunoprecipitated using either anti-CDK4 or anti-CDK6 antibodies. Cell lysis and immunoprecipitation were as described above. HaCaT cultures treated with TGF-β in parallel were stained with DAPI and analyzed by FACS. For 8 hours following TGF-β addition, there was no appreciable change in the percentage of $G_1$ cells. After fourteen hours, the $G_1$ population began to increase. Arrest of HaCaT cells in $G_1$ (approx. 85% $G_1$ cells) required at least 24 hours after treatment of an asynchronous culture.

EXAMPLE 8

TGF-β Treatment Induces p15 mRNA

Asynchronous HaCaT cultures were treated with TGF-β for the indicated times. Total RNA was prepared from treated cells and used for Northern blotting with a probe specific for p15 (e.g. probes consisted of the first coding exons of this genes and was prepared by PCR). Hybridization used for northern blots consisted of 200 mM $NaPO_4$, pH 7.0, 1 mM EDTA, 15% Formamide, 7% SDS, 0.1% bovine serum albumin at 65° C.; wash: 0.2×SSC, 65° C. The p15 probe recognized three p15 mRNAs of approximately 0.8, 2.2 and 3.2 Kb. Northern signals were quantitated on a Fuji BAS2000 phosphorimager and plotted to give a graphical representation of the results. RNA amounts were normalized by mass, and over-probing of the blot with a human actin probe suggested no more than 10% variance in RNA amounts between lanes.

RNAs identical to those used in p15 probe panel were also probed with a fragment specific for p16. Furthermore, RNA from TGF-β treated HaCaT cells was probed oligonucleotides derived from either a fragment of human CDK4 coding sequence or a fragment of the p27 cDNA.

EXAMPLE 9

Generating a Transgenic Mouse pi 3.5 Knockout

The disruptive construct is formed by the two DNA regions of approx. 3–4 Kb flanking the p13.5 gene. These DNA pieces are cloned at both sides of a gene marker that will be used to select the mouse embryonal stem (ES) cells that have incorporated this DNA after transfection. Regions which are homologous to the p16 locus are in turn flanked by another marker which allows selection against cells which have incorporated the disruption vector by non-homologous recombination (e.g. at a locus other than that of the mouse p13.5 gene). Those cells where insertion has occurred in the appropriate position are injected into mouse blastocytes and implanted into the appropriate female mice following standard protocols (*Manipulating the Mouse Embryo*, (Cold Spring Harbor Laboratory Press, Cold Spring Harbor, N.Y., 1986; and Jaenisch (1988) *Science* 240:1468–1474.)

Chimeric pups resulting from the engineered blastocysts can be identified by a coat color marker specific to the transfected ES cells (agouti). Mice with high degrees of chimerism are crossed to identify those with chimeric germ lines and to generate non-chimeric heterozygous disruptants. Homozygous disruptants are derived by breeding the non-chimeric heterozygotes.

EXAMPLE 10

Characterization of CCR-insensitive CDK4 Mutants

A mutant of CDK4 was discovered in cells from a melanoma patient, and the sequence of the mutant enzyme was determined. From the sequence, it was determined that that the gene contained a Arg→Cys at position 24 (see SEQ ID No. 9).

We reisolated the mutant by cloning CDK4 (see Matsushime et al. (1992) *Cell* 71:323–334) and generated a the Cysteine mutation by oligonucleotide primer mutagenesis. To characterize the effect of the mutation, we compared the mutant and wild-type enzyme based on a number of different criteria, including intrinsic activity (e.g. did the mutant constitutively activate CDK4), as well as the ability of other regulatory proteins to control CDK4 activation. Briefly, we generated a series of baculovirus expression systems for overexpressing various proteins. In particular, Sf9 cell lysates (Desai et al. (1992) *Mol Cell Biol* 3:571–582, and Example 6 above) were obtained for mutant and wild-type CDK4, cyclin D1, p16, p15, p21 and p27 (see Polyak et al. (1994) *Genes Dev* 8:9–22; and Toyoshima et al. (1994) *Cell* 78:67–74). Using a GST-RB fusion protein (Example 6) as a substrate for detecting CDK4 kinase activity, various combinations of lysate were lixed and tested for CDK4 activation/inhibition.

When the mutant CDK4 was expressed alone in Sf9 cells, no appreciable phosphorylation of the RB substrate was detected, as is also the case with the wild-type enzyme, indicating that the mutation did cause constitutive acitvation of CDK4. Overexpression of a CDK4 and cyclin D1 in an Sf9 lysate was also identical for both mutant and wild-type kinase, as each was shown to be activated in the presence of cyclin D1. However, upon addition of increasing amounts of either p16- or p15-containing lysate to the CDK4/cyclin D mixture, the wild-type CDK4 was inhibited yet the mutant CDK4 was relatively unaffected, indicating that the mutation gave rise to kinase whose activity is insensitive to either p15 or p16. Furthermore, immunoprecipitation demonstrated that neither p15 or p16 were capable of binding the mutant, as they were apparently lost from the complex which is ordinarily seen with the wild-type CDK4. Finally, similar experiments carried out with p21 and p27 indicated that the particular mutation, Arg24-Cys, did not effect the binding or inhibitory ability of either of those proteins. An analogous mutation to Arg31 of CDK6 (SEQ ID No. 10; and Bates et al. (1994) *Oncogene* 9:71–79 for the wild-type gene) is expected to have the same effect.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 994 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 41..508

(xi) SEQUENCE DESCRIPTION: SEQ ID NO:1:

```
CGGAGAGGGG GAGAACAGAC AACGGGCGGC GGGGAGCAGC ATG GAT CCG GCG GCG        55
                                            Met Asp Pro Ala Ala
                                             1               5

GGG AGC AGC ATG GAG CCT TCG GCT GAC TGG CTG GCC ACG GCC GCG GCC       103
Gly Ser Ser Met Glu Pro Ser Ala Asp Trp Leu Ala Thr Ala Ala Ala
             10                  15                  20

CGG GGT CGG GTA GAG GAG GTG CGG GCG CTG CTG GAG GCG GTG GCG CTG       151
Arg Gly Arg Val Glu Glu Val Arg Ala Leu Leu Glu Ala Val Ala Leu
         25                  30                  35

CCC AAC GCA CCG AAT AGT TAC GGT CGG AGG CCG ATC CAG GTC ATG ATG       199
Pro Asn Ala Pro Asn Ser Tyr Gly Arg Arg Pro Ile Gln Val Met Met
     40                  45                  50

ATG GGC AGC GCC CGA GTG GCG GAG CTG CTG CTG CTC CAC GGC GCG GAG       247
Met Gly Ser Ala Arg Val Ala Glu Leu Leu Leu Leu His Gly Ala Glu
 55                  60                  65

CCC AAC TGC GCC GAC CCC GCC ACT CTC ACC CGA CCC GTG CAC GAC GCT       295
Pro Asn Cys Ala Asp Pro Ala Thr Leu Thr Arg Pro Val His Asp Ala
 70                  75                  80                  85

GCC CGG GAG GGC TTC CTG GAC ACG CTG GTG GTG CTG CAC CGG GCC GGG       343
Ala Arg Glu Gly Phe Leu Asp Thr Leu Val Val Leu His Arg Ala Gly
                 90                  95                 100

GCG CGG CTG GAC GTG CGC GAT GCC TGG GGC CGT CTG CCC GTG GAC CTG       391
Ala Arg Leu Asp Val Arg Asp Ala Trp Gly Arg Leu Pro Val Asp Leu
            105                 110                 115

GCT GAG GAG CTG GGC CAT CGC GAT GTC GCA CGG TAC CTG CGC GCG GCT       439
Ala Glu Glu Leu Gly His Arg Asp Val Ala Arg Tyr Leu Arg Ala Ala
        120                 125                 130

GCG GGG GGC ACC AGA GGC AGT AAC CAT GCC CGC ATA GAT GCC GCG GAA       487
Ala Gly Gly Thr Arg Gly Ser Asn His Ala Arg Ile Asp Ala Ala Glu
    135                 140                 145

GGT CCC TCA GAC ATC CCC GAT TGAAAGAACC AGAGAGGCTC TGAGAAACCT          538
Gly Pro Ser Asp Ile Pro Asp
150                 155

CGGGAAACTT AGATCATCAG TCACCGAAGG TCCTACAGGG CCACAACTGC CCCCGCCACA     598

ACCCACCCCG CTTTCGTAGT TTTCATTTAG AAAATAGAGC TTTTAAAAAT GTCCTGCCTT     658

TTAACGTAGA TATAAGCCTT CCCCCACTAC CGTAAATGTC CATTTATATC ATTTTTTATA     718

TATTCTTATA AAAATGTAAA AAAGAAAAAC ACCGCTTCTG CCTTTTCACT GTGTTGGAGT     778

TTTCTGGAGT GAGCACTCAC GCCCTAAGCG CACATTCATG TGGGCATTTC TTGCGAGCCT     838

CGCAGCCTCC GGAAGCTGTC GACTTCATGA CAAGCATTTT GTGAACTAGG GAAGCTCAGG     898
```

-continued

```
GGGGTTACTG GCTTCTCTTG AGTCACACTG CTAGCAAATG GCAGAACCAA AGCTCAAATA      958

AAAATAAAAT TATTTTCATT CATTCACTCA AAAAAA                                994
```

(2) INFORMATION FOR SEQ ID NO:2:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Pro Ala Ala Gly Ser Ser Met Glu Pro Ser Ala Asp Trp Leu
 1               5                  10                  15

Ala Thr Ala Ala Ala Arg Gly Arg Val Glu Val Arg Ala Leu Leu
                20                  25                  30

Glu Ala Val Ala Leu Pro Asn Ala Pro Asn Ser Tyr Gly Arg Arg Pro
             35                  40                  45

Ile Gln Val Met Met Met Gly Ser Ala Arg Val Ala Glu Leu Leu Leu
 50                  55                  60

Leu His Gly Ala Glu Pro Asn Cys Ala Asp Pro Ala Thr Leu Thr Arg
 65                  70                  75                  80

Pro Val His Asp Ala Ala Arg Glu Gly Phe Leu Asp Thr Leu Val Val
                 85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
                115                 120                 125

Tyr Leu Arg Ala Ala Ala Gly Gly Thr Arg Gly Ser Asn His Ala Arg
130                 135                 140

Ile Asp Ala Ala Glu Gly Pro Ser Asp Ile Pro Asp
145                 150                 155
```

(2) INFORMATION FOR SEQ ID NO:3:

(i) SEQUENCE CHARACTERISTICS:
        (A) LENGTH: 837 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 328..738

(xi) SEQUENCE DESCRIPTION: SEQ ID NO:3:

```
GAGGACTCCG CGACGGTCCG CACCCTGCGG CCAGAGCGGC TTTGAGCTCG GCTGCTTCCG      60

CGCTAGGCGC TTTTTCCCAG AAGCAATCCA GGCGCGCCCG CTGGTTCTTG AGCGCCAGGA     120

AAAGCCCGGA GCTAACGACC GGCCGCTCGG CACTGCACGG GGCCCCAAGC CGCAGAAGAA     180

GGACGACGGG AGGGTAATGA AGCTGAGCCC AGGTCTCCTA GGAAGGAGAG AGTGCGCCGG     240

AGCAGCGTGG GAAAGAAGGG AAGAGTGTCG TTAAGTTTAC GGCCAACGGT GGATTATCCG     300

GGCCGCTGCG CGTCTGGGGG CTGCGGA ATG CGC GAG GAG AAC AAG GGC ATG          351
                                Met Arg Glu Glu Asn Lys Gly Met
                                  1               5

CCC AGT GGG GGC GGC AGC GAT GAG GGT CTG GCC ACG CCG GCG CGG GGA       399
Pro Ser Gly Gly Gly Ser Asp Glu Gly Leu Ala Thr Pro Ala Arg Gly
        10                  15                  20
```

-continued

```
CTA GTG GAG AAG GTG CGA CAC TCC TGG GAA GCC GGC GCG GAT CCC AAC        447
Leu Val Glu Lys Val Arg His Ser Trp Glu Ala Gly Ala Asp Pro Asn
     25                  30                  35                  40

GGA GTC AAC CGT TTC GGG AGG CGC GCG ATC CAG GTC ATG ATG ATG GGC        495
Gly Val Asn Arg Phe Gly Arg Arg Ala Ile Gln Val Met Met Met Gly
                 45                  50                  55

AGC GCC CGC GTG GCG GAG CTG CTG CTG CTC CAC GGC GCG GAG CCC AAC        543
Ser Ala Arg Val Ala Glu Leu Leu Leu Leu His Gly Ala Glu Pro Asn
             60                  65                  70

TGC GCA GAC CCT GCC ACT CTC ACC CGA CCG GTG CAT GAT GCT GCC CGG        591
Cys Ala Asp Pro Ala Thr Leu Thr Arg Pro Val His Asp Ala Ala Arg
         75                  80                  85

GAG GGC TTC CTG GAC ACG CTG GTG GTG CTG CAC CGG GCC GGG GCG CGG        639
Glu Gly Phe Leu Asp Thr Leu Val Val Leu His Arg Ala Gly Ala Arg
     90                  95                  100

CTG GAC GTG CGC GAT GCC TGG GGT CGT CTG CCC GTG GAC TTG GCC GAG        687
Leu Asp Val Arg Asp Ala Trp Gly Arg Leu Pro Val Asp Leu Ala Glu
105                 110                 115                 120

GAG CGG GGC CAC CGC GAC GTT GCA GGG TAC CTG CGC ACA GCC ACG GGG        735
Glu Arg Gly His Arg Asp Val Ala Gly Tyr Leu Arg Thr Ala Thr Gly
                 125                 130                 135

GAC TGACGCCAGG TTCCCCAGCC GCCCACAACG ACTTTATTTT CTTACCCAAT             788
Asp

TTCCCACCCC CACCCACCTA ATTCGATGAA GGCTGCCAAC GGGGAGCGG                  837
```

(2) INFORMATION FOR SEQ ID NO:4:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:4:

```
Met Arg Glu Glu Asn Lys Gly Met Pro Ser Gly Gly Gly Ser Asp Glu
 1               5                  10                  15

Gly Leu Ala Thr Pro Ala Arg Gly Leu Val Glu Lys Val Arg His Ser
             20                  25                  30

Trp Glu Ala Gly Ala Asp Pro Asn Gly Val Asn Arg Phe Gly Arg Arg
         35                  40                  45

Ala Ile Gln Val Met Met Met Gly Ser Ala Arg Val Ala Glu Leu Leu
     50                  55                  60

Leu Leu His Gly Ala Glu Pro Asn Cys Ala Asp Pro Ala Thr Leu Thr
 65                  70                  75                  80

Arg Pro Val His Asp Ala Ala Arg Glu Gly Phe Leu Asp Thr Leu Val
                 85                  90                  95

Val Leu His Arg Ala Gly Ala Arg Leu Asp Val Arg Asp Ala Trp Gly
             100                 105                 110

Arg Leu Pro Val Asp Leu Ala Glu Glu Arg Gly His Arg Asp Val Ala
         115                 120                 125

Gly Tyr Leu Arg Thr Ala Thr Gly Asp
     130                 135
```

(2) INFORMATION FOR SEQ ID NO:5:

(i) SEQUENCE CHARACTERISTICS:
        (A) LENGTH: 853 base pairs
        (B) TYPE: nucleic acid
        (C) STRANDEDNESS: both (D) TOPOLOGY: linear (ii) MOLECULE TYPE: cDNA (ix) FEATURE:
        (A) NAME/KEY: CDS
        (B) LOCATION: 213..587

(xi) SEQUENCE DESCRIPTION: SEQ ID NO:5:

```
GGAGTACAGC AGCGGGAGCA TGGGTCGCAG GTTCTTGGTC ACTGTAAGGA TTCAGCGCGC        60

GGGCCGCCCA CTCCAAGAGA GGGTTTTCTT GGTGAAGTTC GTGCGATCCC GGAGACCCAG       120

GACAGCGAGC TGCGCTCTGG CTTTCGTGAA CATGTTGTTG AGGCTAGAGA GGATCTTGAG       180

AAGAGGGCCG CACCGGAATC CTGGACCAGG TG ATG ATG ATG GGC AAC GTT CAC        233
                                   Met Met Met Gly Asn Val His
                                    1               5

GTA GCA GCT CTT CTG CTC AAC TAC GGT GCA GAT TCG AAC TGC GAG GAC        281
Val Ala Ala Leu Leu Leu Asn Tyr Gly Ala Asp Ser Asn Cys Glu Asp
         10                  15                  20

CCC ACT ACC TTC TCC CGC CCG GTG CAC GAC GCA GCG CGG GAA GGC TTC        329
Pro Thr Thr Phe Ser Arg Pro Val His Asp Ala Ala Arg Glu Gly Phe
     25                  30                  35

CTG GAC ACG CTG GTG GTG CTG CAC GGG TCA GGG GCT CGG CTG GAT GTG        377
Leu Asp Thr Leu Val Val Leu His Gly Ser Gly Ala Arg Leu Asp Val
 40                  45                  50                  55

CGC GAT GCC TGG GGT CGC CTG CCG CTC GAC TTG GCC CAA GAG CGG GGA        425
Arg Asp Ala Trp Gly Arg Leu Pro Leu Asp Leu Ala Gln Glu Arg Gly
                 60                  65                  70

CAT CAA GAC ATC GTG CGA TAT TTG CGT TCC GCT GGG TGC TCT TTG TGT        473
His Gln Asp Ile Val Arg Tyr Leu Arg Ser Ala Gly Cys Ser Leu Cys
             75                  80                  85

TCC GCT GGG TGG TCT TTG TGT ACC GCT GGG AAC GTC GCC CAG ACC GAC        521
Ser Ala Gly Trp Ser Leu Cys Thr Ala Gly Asn Val Ala Gln Thr Asp
         90                  95                 100

GGG CAT AGC TTC AGC TCA AGC ACG CCC AGG GCC CTG GAA CTT CGC GGC        569
Gly His Ser Phe Ser Ser Ser Thr Pro Arg Ala Leu Glu Leu Arg Gly
    105                 110                 115

CAA TCC CAA GAG CAG AGC TAAATCCGCC TCAGCCCGCC TTTTTCTTCT               617
Gln Ser Gln Glu Gln Ser
120             125

TAGCTTCACT TCTAGCGATG CTAGCGTGTC TAGCATGTGG CTTTAAAAAA TACATAATAA      677

TGCTTTTTTT GCAATCACGG GAGGGAGCAG AGGGAGGGAG CAGAAGGAGG GAGGGAGGGA      737

GGGAGGGACC TGGACAGGAA AGGAATGGCA TGAGAAACTG AGCGAAGGCG GCCGCGAAGG      797

GAATAATGGC TGGATTGTTT AAAAAAATAA AATAAAGATA CTTTTTAAAA TGTCAA         853
```

(2) INFORMATION FOR SEQ ID NO:6:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO:6:

```
Met Met Met Gly Asn Val His Val Ala Ala Leu Leu Leu Asn Tyr Gly
 1               5                  10                  15

Ala Asp Ser Asn Cys Glu Asp Pro Thr Thr Phe Ser Arg Pro Val His
             20                  25                  30

Asp Ala Ala Arg Glu Gly Phe Leu Asp Thr Leu Val Val Leu His Gly
         35                  40                  45
```

```
Ser Gly Ala Arg Leu Asp Val Arg Asp Ala Trp Gly Arg Leu Pro Leu
        50                  55                  60

Asp Leu Ala Gln Glu Arg Gly His Gln Asp Ile Val Arg Tyr Leu Arg
 65                  70                  75                  80

Ser Ala Gly Cys Ser Leu Cys Ser Ala Gly Trp Ser Leu Cys Thr Ala
                 85                  90                  95

Gly Asn Val Ala Gln Thr Asp Gly His Ser Phe Ser Ser Thr Pro
                100                 105                 110

Arg Ala Leu Glu Leu Arg Gly Gln Ser Gln Glu Gln Ser
            115                 120                 125
```

(2) INFORMATION FOR SEQ ID NO:7:

(i) SEQUENCE CHARACTERISTICS:
        (A) LENGTH: 231 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..231

(xi) SEQUENCE DESCRIPTION: SEQ ID NO:7:

```
GCA CTC CTG GAA GCC GGC GCA GAT CCC AAC GCC CTG AAC CGC TTC GGG    48
Ala Leu Leu Glu Ala Gly Ala Asp Pro Asn Ala Leu Asn Arg Phe Gly
 1               5                  10                  15

AGG CGC CCA ATC CAG GTC ATG ATG ATG GGC AGC GCC AGG GTG GCA GAG    96
Arg Arg Pro Ile Gln Val Met Met Met Gly Ser Ala Arg Val Ala Glu
                20                  25                  30

CTG CTG CTG CTC CAC GGA GCA GAA CCC AAC TGC GCC GAC CCT GCC ACC   144
Leu Leu Leu Leu His Gly Ala Glu Pro Asn Cys Ala Asp Pro Ala Thr
             35                  40                  45

CTT ACC AGA CCT GTG CAC GAC GCA GCT CGG GAA GGC TTC CTG GAC ACG   192
Leu Thr Arg Pro Val His Asp Ala Ala Arg Glu Gly Phe Leu Asp Thr
         50                  55                  60

CTT GTC GTG CTG CAC CGG GCA GGG GCG CGG TTG GAT GTG                231
Leu Val Val Leu His Arg Ala Gly Ala Arg Leu Asp Val
 65                  70                  75
```

(2) INFORMATION FOR SEQ ID NO:8:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO:8:

```
Ala Leu Leu Glu Ala Gly Ala Asp Pro Asn Ala Leu Asn Arg Phe Gly
 1               5                  10                  15

Arg Arg Pro Ile Gln Val Met Met Met Gly Ser Ala Arg Val Ala Glu
                20                  25                  30

Leu Leu Leu Leu His Gly Ala Glu Pro Asn Cys Ala Asp Pro Ala Thr
             35                  40                  45

Leu Thr Arg Pro Val His Asp Ala Ala Arg Glu Gly Phe Leu Asp Thr
         50                  55                  60

Leu Val Val Leu His Arg Ala Gly Ala Arg Leu Asp Val
 65                  70                  75
```

(2) INFORMATION FOR SEQ ID NO:9:

(i) SEQUENCE CHARACTERISTICS:
        (A) LENGTH: 303 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:9:

```
Met Ala Thr Ser Arg Tyr Glu Pro Val Ala Glu Ile Gly Val Gly Ala
 1               5                  10                  15

Tyr Gly Thr Val Tyr Lys Ala Xaa Asp Pro His Ser Gly His Phe Val
             20                  25                  30

Ala Leu Lys Ser Val Arg Val Pro Asn Gly Gly Gly Gly Gly Gly Gly
         35                  40                  45

Leu Pro Ile Ser Thr Val Arg Glu Val Ala Leu Leu Arg Arg Leu Glu
     50                  55                  60

Ala Phe Glu His Pro Asn Val Val Arg Leu Met Asp Val Cys Ala Thr
 65                  70                  75                  80

Ser Arg Thr Asp Arg Glu Ile Lys Val Thr Leu Val Phe Glu His Val
                 85                  90                  95

Asp Gln Asp Leu Arg Thr Tyr Leu Asp Lys Ala Pro Pro Pro Gly Leu
            100                 105                 110

Pro Ala Glu Thr Ile Lys Asp Leu Met Arg Gln Phe Leu Arg Gly Leu
            115                 120                 125

Asp Phe Leu His Ala Asn Cys Ile Val His Arg Asp Leu Lys Pro Glu
130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
            195                 200                 205

Arg Arg Lys Pro Leu Phe Cys Gly Asn Ser Glu Ala Asp Gln Leu Gly
210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
275                 280                 285

Ala Leu Gln His Ser Tyr Leu His Lys Asp Glu Gly Asn Pro Glu
290                 295                 300
```

(2) INFORMATION FOR SEQ ID NO:10:

(i) SEQUENCE CHARACTERISTICS:
        (A) LENGTH: 326 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:10:

```
Met Glu Lys Asp Gly Leu Cys Arg Ala Asp Gln Gln Tyr Glu Cys Val
1               5                   10                  15

Ala Glu Ile Gly Glu Gly Ala Tyr Gly Lys Val Phe Lys Ala Xaa Asp
                20                  25                  30

Leu Lys Asn Gly Gly Arg Phe Val Ala Leu Lys Arg Val Arg Val Gln
            35                  40                  45

Thr Gly Glu Glu Gly Met Pro Leu Ser Thr Ile Arg Glu Val Ala Val
    50                  55                  60

Leu Arg His Leu Glu Thr Phe Glu His Pro Asn Val Val Arg Leu Phe
65                  70                  75                  80

Asp Val Cys Thr Val Ser Arg Thr Asp Arg Glu Thr Lys Leu Thr Leu
                85                  90                  95

Val Phe Glu His Val Asp Gln Asp Leu Thr Thr Tyr Leu Asp Lys Val
                100                 105                 110

Pro Glu Pro Gly Val Pro Thr Glu Thr Ile Lys Asp Met Met Phe Gln
            115                 120                 125

Leu Leu Arg Gly Leu Asp Phe Leu His Ser His Arg Val Val His Arg
130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
                180                 185                 190

Gln Ser Ser Tyr Ala Thr Pro Val Asp Leu Trp Ser Val Gly Cys Ile
            195                 200                 205

Phe Ala Glu Met Phe Arg Arg Lys Pro Leu Phe Arg Gly Ser Ser Asp
210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
            275                 280                 285

Ile Ser Ala Tyr Ser Ala Leu Ser His Pro Tyr Phe Gln Asp Leu Glu
290                 295                 300

Arg Cys Lys Glu Asn Leu Asp Ser His Leu Pro Pro Ser Gln Asn Thr
305                 310                 315                 320

Ser Glu Leu Asn Thr Ala
            325
```

(2) INFORMATION FOR SEQ ID NO:11:

(i) SEQUENCE CHARACTERISTICS:
        (A) LENGTH: 85 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

```
Met Met Met Gly Xaa Xaa Xaa Val Ala Xaa Leu Leu Leu Xaa Xaa Gly
1               5                   10                  15

Ala Xaa Xaa Asn Cys Xaa Asp Pro Xaa Thr Xaa Xaa Xaa Arg Pro Val
            20              25                  30

His Asp Ala Ala Arg Glu Gly Phe Leu Asp Thr Leu Val Val Leu His
        35                  40              45

Xaa Xaa Gly Ala Arg Leu Asp Val Arg Asp Ala Trp Gly Arg Leu Pro
    50              55              60

Xaa Asp Leu Ala Xaa Glu Xaa Gly His Xaa Asp Xaa Xaa Xaa Tyr Leu
65              70              75                  80

Arg Xaa Ala Xaa Gly
            85
```

We claim:

1. An isolated nucleic acid encoding a polypeptide including an INK4 amino acid sequence which specifically binds to and inhibits a cyclin-dependent kinase (CDK), wherein said nucleic acid comprises a nucleotide sequence which hybridizes at conditions of 2×SSC at 50° C. or higher stringency to a nucleic acid sequence of SEQ ID No: 1, and wherein said polypeptide includes at least four ankyrin-like amino acid sequences.

2. The nucleic acid of claim 1, wherein the polypeptide encoded by said nucleic acid functions as an antagonist of cell cycle progression.

3. The nucleic acid of claim 1, further comprising a transcriptional regulatory sequence operably linked to a nucleotide sequence encoding said polypeptide so as to render said nucleic acid suitable for use as an expression vector.

4. An expression vector, capable of replicating in at least one of a prokaryotic cell and eukaryotic cell, comprising the nucleic acid of claim 1.

5. The expression vector of claim 4, which is a viral vector.

6. The expression vector of claim 5, wherein the viral vector is selected from the group consisting of a retroviral vector, an adeno-associated viral vector, a herpes simplex viral vector, and a vaccinia viral vector.

7. A host cell transfected with the expression vector of claim 4 and expressing said polypeptide.

8. The nucleic acid of claim 1, wherein said polypeptide encoded by said nucleotide sequence has an amino acid sequence represented in SEQ ID No: 2.

9. The nucleic acid of claim 1, wherein the full-length form of said polypeptide has an approximate molecular weight in the range of about 14.5 kD to 16 kD.

10. The nucleic acid of claim 1, wherein said CDK is a $G_1$ phase cyclin.

11. The nucleic acid of claim 10, wherein said CDK is CDK4.

12. An isolated nucleic acid encoding a polypeptide including an INK4 amino acid sequence wherein the nucleic acid comprises a nucleotide sequence which hybridizes at conditions of 2×SSC at 50° C. or higher stringency to a nucleic acid sequence of SEQ ID No: 1 wherein said nucleotide sequence is operably linked to a transcriptional regulatory sequence in an open reading frame and translatable to a polypeptide which binds to a cyclin dependent kinase.

13. The nucleic acid of claim 12, which nucleotide sequence is derived from a cDNA clone.

14. The nucleic acid of claim 12, which nucleotide sequence includes at least one intronic nucleotide sequence disrupting said open reading frame.

15. The nucleic acid of claim 12, wherein said CDK is a $G_1$ phase cyclin.

16. The nucleic acid of claim 15, wherein said CDK is CDK4.

17. The nucleic acid of claim 12, wherein said polypeptide encoded by said nucleic acid includes at least four ankyrin-like repeats.

18. A nucleic acid composition comprising a substantially purified oligonucleotide at least 10–100 base pairs in length, which oligonucleotide is complementary to and which hybridizes under conditions of 2×SSC at 50° C. or higher stringency to sense or antisense sequence of a nucleic acid encoding a human p16 polypeptide, or naturally occurring mutants thereof wherein said human p16 polypeptide specifically binds to a cyclin dependent kinase.

19. The nucleic acid composition of claim 18, said oligonucleotide further comprising a label group attached thereto and able to be detected.

20. The nucleic acid composition of claim 18, wherein said label group is selected from a group consisting of radioisotopes, fluorescent compounds, enzymes, and enzyme co-factors.

21. The nucleic acid composition of claim 18, wherein said label group is selected from the group consisting of radioisotopes, fluorescent compounds, enzymes, and enzyme co-factors.

22. The nucleic acid composition of claim 18, wherein said human p16 polypeptide is characterized as including ankyrin-like repeats.

23. The nucleic acid composition of claim 18, wherein said oligonucleotide includes at least 40 consecutive nucleotides which hybridizes to a sense or antisense sequence of SEQ ID No: 1.

24. The nucleic acid composition of claim 18, wherein said oligonucleotide hybridizes under stringent conditions to the p16 nucleotide sequence designated by SEQ ID No: 1, and which oligonucleotide can specifically detect a p16-encoding nucleic acid sequence.

25. The nucleic acid composition of claim 18, wherein hybridization of said oligonucleotide to a nucleic acid encoding a human p16 protein inhibits transcription or translation of said nucleic acid.

26. The nucleic acid composition of claim 18, wherein said oligonucleotide is resistant to endogenous nuclease cleavage.

27. A recombinant transfection system, comprising
(i) a gene construct comprising a nucleic acid sequence which hybridizes at conditions of 2×SSC at 50° C. or higher stringency to a nucleic acid sequence of SEQ ID No: 1, wherein said construct encodes a polypeptide including an INK4 amino acid sequence and is operably linked to a transcriptional regulatory sequence for causing expression of the polypeptide in eukaryotic cells, the polypeptide being characterized by an ability to bind to and inhibit activation of cyclin dependent kinase (CDK), and
(ii) a gene delivery composition for delivering the gene construct to a cell and causing the cell to be transfected with said gene construct.

28. The recombinant transfection system of claim 27, wherein the gene delivery composition is selected from a group consisting of a recombinant viral particle, a liposome, and a poly-cationic nucleic acid binding agent.

29. The recombinant transfection system of claim 27, wherein the polypeptide comprises four ankyrin-like repeats.

30. The recombinant transfection system of claim 27, wherein the polypeptide comprises an amino acid sequence represented in SEQ ID No: 2.

31. The recombinant transfection system of claim 27, wherein said CDK is a $G_1$ phase cyclin.

32. The recombinant transfection system of claim 31, wherein said CDK is CDK4.

33. The recombinant transfection system of claim 27, wherein the gene construct is provided as a viral vector.

34. The recombinant transfection system of claim 33, wherein the viral vector is selected from the group consisting of a retroviral vector, an adeno-associated viral vector, a herpes simplex viral vector, and a vaccinia viral vector.

35. An isolated nucleic acid comprising a nucleotide sequence encoding a human p16 polypeptide, which polypeptide specifically binds a cyclin-dependent kinase (CDK).

36. An isolated nucleic acid comprising a nucleotide sequence which hybridizes under conditions of 2×SSC at 50° C. or higher stringency to a human p16 gene and which encodes a polypeptide that specifically binds a cyclin-dependent kinase (CDK).

37. An isolated recombinant gene comprising a nucleotide sequence encoding a human p16 polypeptide having ankyrin-like repeats and capable of binding a cyclin dependent kinase, said nucleotide sequence being operably linked to a transcriptional regulatory sequence in an open reading frame and translatable to said human p16 polypeptide.

38. The recombinant gene of claim 37, wherein said human p16 polypeptide is a fusion functional in a two-hybrid screening assay protein.

39. The recombinant gene of claim 37, wherein said human p16 polypeptide is designated by SEQ ID No: 2.

40. A method of producing a recombinant peptide comprising culturing the cell of claim 7 in a cell culture medium to express said polypeptide and isolating said polypeptide from said cell culture.

* * * * *